(12) United States Patent
Tallant et al.

(10) Patent No.: US 7,375,073 B2
(45) Date of Patent: May 20, 2008

(54) ANGIOTENSIN-(1-7) AND ANGIOTENSIN-(1-7) AGONISTS FOR INHIBITION OF CANCER CELL GROWTH

(75) Inventors: E. Ann Tallant, Lewisville, NC (US); Patricia E. Gallagher, Lewisville, NC (US); Carlos M. Ferrario, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 52 days.

(21) Appl. No.: 10/375,733

(22) Filed: Feb. 27, 2003

(65) Prior Publication Data

US 2003/0203834 A1 Oct. 30, 2003

Related U.S. Application Data

(60) Provisional application No. 60/359,847, filed on Feb. 27, 2002.

(51) Int. Cl.
*A61K 38/00* (2006.01)
*G01N 33/53* (2006.01)
(52) U.S. Cl. ............................. 514/2; 514/1; 434/7.1
(58) Field of Classification Search ................ 514/2
See application file for complete search history.

(56) References Cited

U.S. PATENT DOCUMENTS

| | | | |
|---|---|---|---|
| 6,235,766 B1 | 5/2001 | Heitsch et al. | |
| 6,239,109 B1* | 5/2001 | Rodgers et al. | 514/14 |
| 6,429,222 B2 | 8/2002 | Heitsch et al. | |
| 6,455,500 B1* | 9/2002 | Rodgers et al. | 514/16 |
| 7,122,523 B2 | 10/2006 | Rodgers et al. | |
| 2001/0018449 A1 | 8/2001 | Heitsch et al. | |
| 2004/0176302 A1* | 9/2004 | Rodgers et al. | 514/16 |

FOREIGN PATENT DOCUMENTS

| | | |
|---|---|---|
| WO | WO 99/40106 | 8/1999 |
| WO | WO 02/087504 A2 | 11/2002 |
| WO | WO 03/039434 A2 | 5/2003 |

OTHER PUBLICATIONS

Parsons, Peptide Hormones, University Park Press, Jun. 1976, p. 1-7.*
Online-Medical Dictionary. "Amino acid". http://cancerweb.ncl.ac.uk/cgi-bin/omd?query=amino+acid. Nov. 13, 1997 (complete reference available online).*
P. Ambuhl, et al. Effects of angiotensin analogues and angiotensin receptor antagonists on paraventricular neurones. *Regul.Pept.* 1992;38:111-120.
R. G. Appel. Mechanisms of atrial natiuretic factor-induced inhibition of rat mesangial cell mitogenesis. *Am.J.Physiol.* 1990;259:E312-E318.
Y. Asada, et al. Inhibitory effects of prostacyclin analogue, TFC-132, an aortic neointimal thickening in vivo and smooth muscle cell proliferation in vitro. *Prostaglandins Leukot.Essen.Fatty Acids.* 1994;51:245-248.
K. L. Barrett, et al., Advances in cytochemical methods for detection of apoptosis. *J.Histochem.Cytochem.* 2001;49:821-832.
I. F. Benter, et al. Cardiovascular actions of angiotensin-(1-7), *Peptides.* 1993;14:679-684.
I. F. Benter, et al. Antihypertensive actions of angiotensin-(1-7) in spontaneously hypertensive rats. *Am.J.Physiol.Heart.Circ.Physiol.* 1995;269:H313-H319.
R. R. Britto, et al. Role of angiotensin-(1-7) in modulation of the baroreflex in renovascular hypertensive rats. *Hypertension.* 1997;30:549-556.
K. B. Brosnihan, et al. Angiotensin-(1-7) dilates canine coronary arteries through kinins and nitric oxide. *Hypertension.* 1996;27:523-528.
F. M. Bumpus, et al. Nomenclature for Angiotensin Receptors. A report of the nomenclature committee of the council for high blood presssure research. *Hypertension.* 1991;17:720-721.
R. M. Carey. Role of the angiotensin $AT_2$ receptor in blood pressure regulation and therapeutic implications. *Am.J.Hypertens.* 2001;14:98-102.
D. J. Campbell, et al. Nephrectomy, converting enzyme inhibition, and angiotensin peptides. *Hypertension.* 1993;22:513-522.
M. C. Chappell, et al. Identification of angiotensin-(1-7) in rat brain: evidence for differential processing of angiotensin peptides. *J.Biol.Chem.* 1989:264:16518-16523.
M. C. Chappell, et al. Characterization of angiotensin II receptor subtypes in pancreatic acinar AR42J cells. *Peptides.* 1995;16:741-747.
M. C. Chappell, et al. Metabolism of angiotensin-(1-7) by angiotensin-converting enzyme. *Hypertension.* 1998;31:362-367.
M. C. Chappell, et al. Processing of angiotensin peptides by NG108-15 neuroblastoma X glioma hybrid cell line. *Peptides.* 1990;11:375-380.

(Continued)

*Primary Examiner*—Cecilia J. Tsang
*Assistant Examiner*—Maury Audet
(74) *Attorney, Agent, or Firm*—Kilpatrick Stockton LLP

(57) ABSTRACT

The present invention describes the use of angiotensin-(1-7) peptide as an anti-cancer therapeutic. Thus, in one embodiment, the present invention comprises a composition to inhibit the growth of cancer cells in an individual comprising a pharmaceutically effective amount of an agonist for the angiotensin-(1-7) receptor to inhibit cancer cell growth or proliferation. Application of a pharmaceutically effective amount of angiotensin-(1-7) or angiotensin-(1-7) receptor agonist is associated with an increase in the expression of genes involved in tumor suppression, apoptosis, and/or cell cycle inhibition, and a decrease the expression of known oncogenes, protein kinases, and/or cell cycle progression genes. Cancers treated using the methods and compositions described herein include cancers having an angiotensin-(1-7) receptor, including, but not limited to, breast and lung cancer.

19 Claims, 16 Drawing Sheets

OTHER PUBLICATIONS

M. C. Chappell, et al. Conversion of angiotensin I to angiotensin-(1-7) by thimet oligopeptidase (E.C.3.4.24.15) in vascular smooth muscle cells. *J Vasc Biol Med*. 1994;5:129-137.

C. E. Clay, et al. Influence of J series prostaglandins on apoptosis and tumorigenesis of breast cancer cells. *Carcinogenesis*. 1999:20:1905-1911.

S. J. Cook, et al., Inhibition by cAMP of Ras-dependent activation of Raf. *Science*. 1993;262:1069-1072.

H. Darius, et al. Effects of ciprostene on restenosis rate during therapeutic transluminal coronary angioplasty. *Prostaglandins in the Cardiovascular System*. 1992;305-311.

M. De Gasparo, et al. Proposed update of angiotensin receptor nomenclature. *Hypertension*. 1995;25:924-927.

A. DelliPizzi, et al. Natriuretic action of angiotensin(1-7). *Br.J. Pharmacol*. 1994;111:1-3.

A. DelliPizzi, et al. Renal actions of Ang-(1-7): Comparison with Ang II. *The Pharmacologist* 34:196. 1992 (Abstract 326).

B. R. Dey, et al. Suppressor of cytokine signaling (SOCS)-3 protein interacts with the insulin-like growth factor-I receptor. *Biochem. Biophys.Res.Commun*. 2000;278:38-43.

R. J. Duhe, et al. Negative regulation of Janus kinases. *Cell Biochem.Biophys*. 2000; 34; 17-59.

D. Felix, et al. Neurophysiological responses to angiotensin-(1-7). *Hypertension*. 1991;17:1111-1114.

A. Fernandes, et al. ErbB-2 kinase is required for constitutive stat 3 activation in malignant human lung epithelial cells. *Int.J.Cancer*. 1999;83:564-570.

C. M. Ferrario, et al. Counterregulatory actions of angiotensin-(1-7). *Hypertension*. 1997;30:535-541.

M. A. P. Fontes, et al. Evidence that angiotensin-(1-7) plays a role in the central control of blood pressure at the ventro-lateral medulla acting through specific receptors. *Brain Res*. 1994:665:175-180.

E. J. Freeman, et al. Angiotensin-(1-7) [Ang-(1-7)] inhibits vascular smooth muscle growth. *Hypertension*. 22, 414. 1993.

E. J. Freeman, et al. Angiotensin-(1-7) inhibits vascular smooth muscle cell growth. *Hypertension*. 1996;28:104-108.

P. E. Gallagher, et al. Estrogen regulation of angiotensin-converting enzyme mRNA. *Hypertension*. 1999;33:323-328.

P. E. Gallagher, et al. Molecular mechanisms for inhibition of human lung cancer cell growth by angiotensin. Proceedings of American Cancer Research; 43:759; Abstract No. 3767 presented at 93rd Annual Meeting Apr. 6-10, 2002, San Franciso.

B. Gao, et al. Constitutive activation of JAK-STAT3 signaling by BRCA1 in human prostate cancer cells. *FEBS Lett*. 2001;488:179-184.

N. H. Garcia, et al. Angiotensin 1-7 has a biphasic effect on fluid absorption in the proximal straight tubule, *J.Am.Soc.Nephrol*. 1994;5:1133-1138.

Garcia, et al. Constitutive activation of Stat3 by the Src and JAK tyrosine kinases participates in growth regulation of human breast carcinoma cells. *Oncogene*. 2001;20:2499-2513.

J. B. Gibbs. Anticancer drug targets: growth factors and growth factor signaling. *J.Clin.Invest*. 2000;105:9-13.

R. J. Gryglewski, et al. Arterial walls are protected against deposition of platelet thrombi by a substance (prostaglandin X) which they make from prostaglandin endoperoxides. *Prostaglandins*. 1976;12:685-713.

R. K. Handa, et al. Renal actions of angiotensin-(1-7) in vivo and in vitro studies. *Am.J.Physiol*. 1996;270:F141-F147.

S. L. Hazen, et al. Suicide inhibition of canine myocardial cytosolic calcium-independent phospholipase $A_2$; mechanism-based discrimination between calcium-dependent and—independent phospholipases $A_2$. *J.Biol.Chem*. 1991;266:7227-7232.

L. E. Heasley. Autocrine and paracrine signaling through neuropeptide receptors in human cancer. *Oncogene*. 2001;20:1563-1569.

H. Heitsch, et al. Angiotensin-(1-7) stimulated release of nitric oxide and superoxide release from endolethial cells. *Hypertension*. 2001;37:72-76.

S. I. Hii, et al. Captopril inhibits tumour growth in a xenograft model of human renal cell carcinoma. *British Journal of Cancer*. 1998;77:880-883.

S. D. Hitchey, et al. Association between the natriuretic action of angiotensin- (1-7) and selective stimulation of renal prostaglandin $I_2$ release. *Hypertension*. 1995;25:1238-1244.

W. C. Hope, et al. Secretory phospholipase $A_2$ inhibitors and calmodulin antagonists as inhibitors of cytosolic phospholipase $A_2$. *Agents Actions*. 1993;39:C39-C42.

S. N. Iyer, et al. Vasodepressor actions of angiotensin-(1-7) unmasked during combined treatment with lisinopril and losartan. *Hypertension*. 1998;31:699-705.

S. N. Iyer et al. Angiotensin-(1-7) contributes to the antihypertensive effects of blockade of the renin-angiotensin system. *Hypertension*. 1998;31:356-361.

S. N. Iyer, et al. Evidence that prostaglandins mediate the antihypertensive actions of angiotensin-(1-7) during chronic blockade of the renin-angiotensin system. *J.Cardiovasc.Pharmacol*. 2000;36:109-117.

N. Jaiswal, et al. Stimulation of endothelial cell prostaglandin production by angiotensin peptides. Characterization of receptors. *Hypertension*. 1992;19[supple II]:II-49—II-55.

N. Jaiswal, et al. Characterization of angiotensin receptors mediating prostaglandin synthesis in C6 glioma cells. *Am.J.Physiol.Regul. Integr.Comp.Physiol*. 1991;260:R1000-R1006.

N. Jaiswal, et al. Alterations in prostaglandin production in spontaneously hypertensive rat smooth muscle cells. *Hypertension*. 1993;21:900-905.

N. Jaiswal, et al. Subtype 2 angiotensin receptors mediate prostaglandin synthesis in human astrocytes. *Hypertension*. 1991;17:1115-1120.

N. Jaiswal, et al. Differential regulation of prostaglandin synthesis by angiotensin peptides in porcine aortic smooth muscle cells: Subtypes of angiotensin receptors involved. *J.Pharmacol.Exp.Ther*. 1993;265:664-673.

H. Jick, et al. Calcium-channel blockers and risk of cancer. *Lancet*. 1997;349:525-528.

Y. Kato, et al. BMK1/ERK5 regulates serum-induced early gene expression through transcription factor MEF2C. *The EMBO Journal*. 1997;16:7054-7066.

Y. Kato, et al. Bmk1/Erk5 is required for cell proliferation induced by epidermal growth factor. *Nature*. 1998;395:713-716.

M. Kibbe, et al. Inducible nitric oxide synthase and vascular injury. *Cardiovas.Res*. 1999;43:650-657.

K. Kohara, et al. Angiotensin-(1-7). A member of circulating angiotensin peptides. *Hypertension*. 1991;17:131-138.

K. Kohara, et al. Angiotensin-(1-7) in the spontaneously hypertensive rat. *Circulation* 84(suppl II), II-662; Abstract No. 2630, 1991.

K. Kohara, et al. Angiotensin-(1-7) in the spontaneously hypertensive rat. *Peptides*. 1993;14:883-891.

A. C. Lawrence, et al. An alternative strategy for the radioimmunoasssay of angiotensin peptides using amino-terminal-directed antisera: measurement of eight angiotensin peptides in human plasma. *J.Hypertens*. 1990;8:715-724.

J. H. Lee, et al. The inhibitory effect of adenovirus-mediated p16INK4a gene transfer on the proliferation of lung cancer cell line. *Anticancer Res*. 1998;18:3257-3261.

A. F. Lever, et al. Do inhibitors of angiotensin-I-converting enzyme protect against risk of cancer? *The Lancet*. 1998;352:179-184.

O. H. Lowry, et al. Protein measurement with the Folin-Phenol reagent. *J.Biol.Chem*. 1951;193:265-275.

J. Lukas, et al. Retinoblastoma-protein-dependent cell-cycle inhibition by the tumor-suppressor p16. *Nature*. 1995;375:503-506.

M. Luque, et al. Effects of captopril related to increased levels of prostacyclin and angiotensin-(1-7) in essential hypertension. *J. Hypertens*. 1996;14:799-805.

Z. T. Madhun, et al. An epoxygenase metabolite of arachidonic acid mediates angiotensin II-induced rises in cytosolic calcium in rabbit proximal tubule epithelial cells. *J.Clin.Invest*. 1991;88:456-461.

A. Mallat, et al. Growth inhibitory properties of endothelin-1 in activated human hepatic stellate cells: A cyclic adenosine monophosphate-mediated pathway. *J.Clin.Invest*. 1996;98:2771-2778.

M. B. Marrero, et al. Role of Janus kinase/signal transducer and activator of transcription and mitogen-activated protein kinase cascades in angiotensin II- and platelet-derived growth factor-induced vascular smooth muscle proliferation. *J.Biol.Chem*. 1997;272:24684-24690.

M. B. Marrero, et al. Direct stimulation of Jak/STAT pathway by the angiotensin II $AT_1$ receptor. *Nature*. 1995;375:247-250.

K. Maruno, et al. Vasoactive intestinal peptide inhibits human small-cell lung cancer proliferation in vitro and in vivo. *Proc.Natl.Acad.Sci.USA*. 1998;95:14373-14378.

E. A. Meade, et al. Differential inhibition of prostaglandin endoperoxide synthase (cyclooxygenase) isozymes by aspirin and other non-steroidal anti-inflammatory drugs. *J.Biol.Chem*. 1993;268:6610-14.

W. Meng, et al. Comparative effects of angiotensin-(1-7) and angiotensin II on piglet pial arterioles. *Stroke*. 1993;24:2041-2045.

C. J. Molloy, et al. Angiotensin II stimulation of rapid protein tyrosine phosphorylation and protein kinase activation in rat aortic smooth muscle cells. *J.Biol.Chem*. 1993;268:7338-7345.

S. Moncada, et al. A lipid peroxide inhibits the enzyme in blood vessel microsomes that generates from prostaglandin endoperoxides the substance (prostaglandin X) which prevents platelet aggregation. *Prostaglandins*. 1976;12:715-733.

M. M. Muthalif, et al. Signal tranduction mechanism involved in angiotensin-(1-7)-stimulated arachidonic acid release and prostanoid synthesis in rabbit aortic smooth muscle cells. *J.Pharmacol.Exp.Ther*. 1998;284:388-398.

H. Nakamoto, et al. Angiotensin-(1-7) and nitric oxide interaction in renovascular hypertension. *Hypertension*. 1995;25:796-802.

D. R. Oliveira, et al. Changes in the baroreflex control of heart rate produced by central infusion of selective angiotensin in hypertensive rats. *Hypertension*. 1998;27:1284-1290.

S. Y. Osei, et al. Differential responses to angiotensin-(1-7) in the feline mesenteric and hindquarters vascular beds. *Eur.J.Pharmacol*. 1993;234:35-42.

M. Pahor, et al. Do calcium blockers increase the risk of cancer? *Am.J.Hypertens*. 1996;9:695-699.

R. D. Paula, et al. Angiotensin-(1-7) potentiates the hyotensive effect of bradykinin in conscious rats. *Hypertension*. 1995;26:1154-1159.

S. L. Pelech, et al. MAP kinases: charting the regulatory pathways. *Science*. 1992;257:1355-1356.

I. Porsti, et al. Release of nitric oxide by angiotensin-(1-7) from porcine coronary endothelium: Implicaitons for a novel angiotensin receptor. *Br.J.Pharmacol* 1994;111:652-654.

F. Ruschitzka, et al. A rationale for treatment of endothelial dysfunction in hypertension. *J Hypertension*. 1999;17;S25-S35.

R. A. S. Santos, et al. Characterization of a new angiotensin antagonist selective for angiotensin-(1-7): Evidence that the actions of angiotensin- (1-7) are mediated by specific angiotensin receptors. *Brain Res.Bull*. 1994;35:293-298.

M. T. Schiavone, et al. Release of vasopressin from the rat hypothalamo-neurohypophysial system by angiotensin-(1-7) heptapeptide. *Proc.Natl.Acad.Sci.USA*. 1988;85:4095-4098.

M. Schirner, et al. Tumor metastasis inhibition with the prostacyclin analogue cicaprost depends on discontinuous plasma peak levels. *Prostaglandins Leukot.Essen.Fatty Acids*. 1998;58:311-317.

M. Serrano, et al. Inhibition of ras-induced proliferation and cellular transformation by p16$^{INK4a}$ *Science*. 1995;267:249-252.

M. Serrano, et al. A new regulatory motif in cell-cycle control causing specific inhibition of cyclinD/CDK4. *Nature*. 1995;366:704-707.

T. Sethi, et al. Growth of small cell lung cancer cells: stimulation by multiple neuropeptides and inhibition by broad spectrum antagonists in vitro and in vivo. *Cancer Res*. 1992;52:2737s-2742.

W. B. Strawn, et al. .Angiotensin-(1-7) reduces smooth muscle growth after vascular injury. *Hypertension*. 1999;33:207-211.

K. Sumitomo, et al. Activation of RB tumor suppressor protein and growth suppression of small cell lung carcinoma cells by reintroduction of p16INK4A gene. *Int.J. Oncol*. 1999;14:1075-1080.

Tallant E. A., et al. Antiproliferative actions of angiotensin-(1-7) in vascular smooth muscle. *Hypertension*. 1999;34:950-957.

E. A. Tallant, et al. Identification and regulation of angiotensin II receptor subtypes on NG108-15 cells. *Hypertension*. 1991;17:1135-1143.

E. A. Tallant, et al. Human astrocytes contain two distinct angiotensin receptor subtypes. *Hypertension*. 1991;18:32-39.

E. A. Tallant, et al. Biology of angiotensin II receptor inhibition with a focus on losartan: a new drug for the treatment of hypertension. *Exp.Opin.Invest.Drugs*. 1996, 5:1201-1214.

E. A. Tallant, et al. Bovine aortic endothelial cells contain an angiotensin-(1-7) receptor. *Hypertension* . 1997;29:388-393.

E. A. Tallant, et al. Attenuation of Human Breast and Lung Cancer Cell Growth by Angiotensin—(1-7). *The FASEB Journal*. 2001;15:4; Abstract 637.7.

E. A. Tallant, et al. Inhibition of Human Lung Cancer Cell Growth by Angiotensin—(1-7). *American Association for Cancer Research*. 92$^{nd}$ Annual Meeting. 2001;vol. 42; Abstract No. 2181.

Y. L. Tran, et al. Angiotensin-(1-7) and the rat aorta: Modulation by the endothelium. *J.Cardiovasc.Pharmacol*. 1997;30:676-682.

A. J. Trimboli, et al. Influence of coenzyme A-independent transacylase and cyclooxygenase inhibitors on the proliferation of breast cancer cells. *Cancer Res*. 1999:59:6171-77.

M. R. Uddin, et al. Cytochrome P-450 metabolites mediate norepinephrine-induced mitogenic signaling. *Hypertension*. 1998;31:242-247.

C. Vickers et al., Hydrolysis of biological peptides by human angiotensin-converting enzyme-related carboxypeptidase. *J.Biol. Chem*. 2002, 227:14838-14843.

B. S. Vishwanath, et al. Interaction of aristolochic acid with *vipera russelli* phospholipase $A_2$; its effect on enzymatic and pathological activities. *Toxicon*. 1987;25:929-937.

J. J. Volpert, et al. *Captopril inhibits angiogenesis and slows the growth of experimental tumors in rats*, J.Clin.Invest. 1996;98:671-679.

H. Wang, et al. Antitumor activity and pharmacokinetics of a mixed-backbone antisense oligonucleotide targeted to the Rialpha subunit of protein kinase A after oral administration. *Proc.Natl.Acad.Sci.USA*. 1999;96:13989-13994.

Y. Wen, et al. Mechanisms of Ang II-induced mitogenic responses: role of 12-lipoxygenase and biphasic MAP kinase. *Am.J.Physiol. Cell Physiol*. 1996;71:C1212-C1220.

M. G. Wilkinson, et al. Control of the eukaryotic cell cycle by MAP kinase signaling pathways. *FASEB J*. 2000;14:2147-2157.

M. C. Willingham. Cytochemical methods for the detection of apoptosis. *J.Histochem.Cytochem*. 1999;47:1101-1109.

J. Wu, et al. Inhibition of EGF-activated MAP kinase signaling pathway by adenosine 3'-5'-monophosphate. *Science*. 1993;262:1065-1068.

O. Yazgan, et al. Differential binding of the menin tumor suppressor protein to JunD isoforms. *Cancer Res*. 2001;61:916-920.

M. R. Young, et al. Regulation of Lewis lung carcinoma invasion and metastasis by protein kinase A. *Int.J.Cancer*, 1995;61:104-109.

Gallagher, P. E. et al., "Inhibition of Human Lung Cancer Cell Growth by Angiotensin-(1-7)," Carcinogenesis, 2004, vol. 25, No. 11, 2045-2052.

Langeveld, B. et al., "Angiotensin-(1-7) Attenuates Neointimal Formation After Stent Implantation in the Rat," *Hypertension*, 2005, vol. 45, 138-141. Hypertension is available at http://www.hypertensionaha.org.

Santos, R. A. S. et al., "Angiotensin-(1-7) is an Endogenous Ligand for the G Protein-Coupled Receptor Mas," Proc. Natl. Acad. Sci., 2003, vol. 100, No. 14, 8258-8263.

Clark, M. et al., "Angiotensin-(1-7) Downregulates the Angiotensin II Type I Receptor in Vascular Smooth Muscle Cells," Hypertension, vol. 37, pp. 1141-1146, 2001.

Iwata, M. et al., "Angiotensin-(1-7) binds to Specific Receptors on Cardiac Fibroblasts to Initiate Antifibrotic and Antitrophic Effects," Am. J. Physiol. Heart Circ. Physiol., vol. 289, pp. H2356-H2363, 2005.

Rodgers, K. et al., "Phase I/II Dose Escalation Study of Angiotensin 1-7 [A(1-7)] Administered Before and After Chemotherapy in Patients with Newly Diagnosed Breast Cancer," Cancer Chemother. Pharmacol., vol. 57, pp. 559-568, 2006.

Yamada, K. et al., "Converting Enzyme Determines Plasma Clearance of Angiotensin-(1-7)," Hypertension, vol. 32, pp. 496-502, 1998.

Santos, R. A.S. et al., "Angiotensin-(1-7): An Update," Regulatory Peptides, vol. 91, pp. 45-62, 2000.

European Search Report mailed Apr. 26, 2006.

Ellefson, D.D. et al., "Synergistic effects of co-administration of angiotensin 1-7 and Neupogen on hematopoietic recovery in mice," *Cancer Chemother Pharmacol* 53:15-24, 2004..

Kono, T.A. et al., "Biological activities of angiotensin II-(1-6)-hexapeptide and agiontensin II-(1-7)-heptapeptide in man," *Life Sci* 38: 1515-9, 1986.

Plovsing, R.R. et al., "Effects of truncated angiotensins in human after double blockade of the renin system," *Am J Physiol Regulatory Integrative Comp Physiol* 285:981-91, 2003.

Tallant, E.A. et al., "Angiotensin-(1-7) inhibits growth of cardiac myocytes through activation of the *mas* receptor," *Am J Physiol Heart Circ Physiol*, 289:H1560-H1566, 2005.

Tallant, E.A. et al., "Molecular Mechanisms of Inhibition of Vascular Growth by Angiotensin-(1-7)," *Hypertension* 42:574-9, 2003.

Ueda, S. et al., "Angiotensin(1-7) potenitates bradykinin-induced vasodilation in man," *J Hypertension* 19:2001-9, 2001.

Welches, W.R. et al., "A comparison of the properties and enzymatic activities of three angiotensin processing enzymes: angiotensin converting enzyme, prolyl endopeptidase and neutral endopeptidase 24.11." *Life Sci* 52:1461-80, 1993.

Welches, W.R. et al., "Evidence that prolyl endopeptidase participates in the processing of brain angiotensin," *J Hypertension* 9:631-8, 1991.

Yamamoto, K. et al., "In Vivo Metabolism of Angiotensin I by Neutral Endopeptidase (EC 3.4.24.11) in Spontaneously Hypertensive Rats," *Hypertension* 19:692-6, 1992.

\* cited by examiner

ANGIOTENSIN-(1-7) AND ANGIOTENSIN-(1-7) AGONISTS FOR INHIBITION OF CANCER CELL GROWTH

CROSS REFERENCE TO RELATED APPLICATIONS

This application claims priority to U.S. Provisional Application Ser. No. 60/359,847, filed Feb. 27, 2002. The disclosure of U.S. Provisional Application Ser. No. 60/359,847 is incorporated herein by reference in its entirety.

FIELD OF THE INVENTION

The present invention relates to compositions and methods for the treatment and prevention of cancer. More specifically, the present invention relates to the use of angiotensin-(1-7) or other agonists for the angiotensin-(1-7) receptor as anticancer therapeutics.

BACKGROUND

Angiotensin-(1-7) [Ang-(1-7)] is an endogenous peptide hormone which is normally present in the circulation at concentrations similar to angiotensin II (Ang II) and is primarily derived from angiotensin I (Ang I) by tissue peptidases, including neprilysin, thimet oligopeptidase and prolyl endopeptidase (Ferrario, C. M. et al., *Hypertension*, 1997, 30:535-541) and by angiotensin converting enzyme (ACE) 2 from angiotensin II (Ang II) (Vickers, C., et al., *J. Biol. Chem.*, 2002, 277:14836-14843). In addition, Ang-(1-7) is a substrate for ACE (Chappell, M. C. et al. *Hypertension*, 1998, 31:362-367). ACE catalyzes the conversion of angiotensin I (Ang I) to the biologically active peptide angiotensin II [Ang II]. Treatment of patients or animals with ACE inhibitors results in a significant elevation in the circulating and tissue levels of Ang II, as well as the N-terminal heptapeptide fragment of Ang II, angiotensin-(1-7) (Campbell, M. C. et al., *Hypertension*, 1993, 22:513-522; Kohara, K. et al., *Hypertension*, 1991, 17:131-138Lawrence, A. C. et al., *J. Hypertens.*, 1990, 8:715-724; and Luque, M. et al., *J. Hypertens.*, 1996, 14:799-805). It has been suggested that ACE inhibition not only elevates Ang-(1-7) by increasing Ang I, the substrate for Ang-(1-7) production, but also by preventing Ang-(1-7) conversion to the inactive fragment Ang-(1-5).

Although Ang-(1-7) was long-considered an inactive product of the degradation of Ang II, studies showed that the heptapeptide produces unique physiological responses which are often opposite to those of the well-recognized angiotensin peptide, Ang II (Ferrario, C. M. et al., *Hypertension*, 1997, 30:535-541). Thus, Ang-(1-7) has been shown to stimulate vasopressin release from neuropeptidergic neurons (Schiavone, M. T. et al., *Proc. Natl. Acad. Sci. USA*, 1988, 85:4095-4098), increase the release of certain neurotransmitters (Ambuhl, P. et al., *Regul. Pept.*, 1992, 38:111-120), reduce blood pressure in hypertensive dogs and rats (Benter, I. F. et al., *Am J. Physiol. Heart Circ. Physiol.*, 1995, 269:H313-H319;and Nakamoto, H. et al., *Hypertension*, 1995, 25:796-802), and have biphasic effects on renal fluid absorption (DelliPizzi, A. et al., *Br. J. Pharmacol.*, 1994, 111:1-3; DelliPizzi, A. et al., *Pharmacologist*, 34, 1992; Garcia, N. H. and Garbin, J. L., *J. Am. Soc. Nephrol.*, 1994, 5:1133-1138; Handa, R. K. et al., *Am. J. Physiol.*, 1996, 270:F141-F147;and Hilchey, S. D. and Bell-Quilley, C. P., *Hypertension*, 1995, 25:1238-1244).

Besides its role in reducing blood pressure, Ang-(1-7) attenuates vascular growth both in vitro and in vivo (Freeman, E. J. et al., *Hypertension*, 1996, 28:104-108; Strawn, W. B. et al., *Hypertension*, 1999, 33:207-211;and Tallant, E. A. et al., *Hypertension*, 1999, 34:950-957). Also, hypertensive patients administered ACE inhibitors show a reduced risk of cancer, particularly lung and sex-specific cancers (Jick, H., et al., *Lancet*, 1997, 349:525-528; Lever, A. F. et al., *Lancet*, 1998, 352:179-184;and Pahor, M. et al., *Am. J. Hypertens.*, 1996, 9:695-699).

What is needed in cancer prevention and therapeutics is a way to prevent tumors from forming, or to inhibit the growth of tumors once formed. Also, what is needed are agents that act specifically at the tumor cell, thus minimizing non-specific and/or toxic side effects. Preferably, the chemotherapeutic agents will comprise ligands that target the chemotherapeutic agent to cancer cells with high efficacy to either reduce cellular signals that promote cell growth, or to increase cellular signals that promote cell death.

SUMMARY OF THE INVENTION

The present invention relates to the use of angiotensin-(1-7) [Ang-(1-7)] receptor agonists as anticancer therapeutics. Thus, embodiments of the present invention describes the use of agonists for the Ang-(1-7) receptor, such as the Ang-(1-7) peptide and derivatives thereof, or agents which increase levels of plasma, tissue or cellular Ang-(1-7), as compounds for prevention and treatment of cancer cell growth and proliferation.

Embodiments of the present invention recognize that Ang-(1-7) can inhibit tumor cell growth in vitro and in vivo. Preferably, cancers treated by the method of the present invention comprise bladder cancer, breast cancer, brain cancer, colon cancer, endometrial cancer, head and neck cancer, leukemia, lymphoma, lung cancer, melanoma, liver cancer, rectal cancer, ovarian cancer, prostate cancer, bone cancer, pancreatic cancer, skin cancer, or renal cancer.

In one embodiment, the present invention comprises a composition for inhibition of cell growth or proliferation comprising a pharmaceutically effective amount of an agonist for the angiotensin-(1-7) receptor in a pharmaceutically acceptable carrier, wherein a pharmaceutically effective amount of angiotensin-(1-7) receptor agonist comprises an amount which is sufficient to inhibit cell growth or proliferation.

In an embodiment, the present invention comprises a composition for inhibition of cancer cell growth or proliferation comprising a pharmaceutically effective amount of an agonist for the angiotensin-(1-7) receptor in a pharmaceutically acceptable carrier, wherein a pharmaceutically effective amount of angiotensin-(1-7) receptor agonist inhibits growth or proliferation of the cancer cells. In an embodiment, the angiotensin-(1-7) receptor agonist comprises angiotensin-(1-7) peptide having the sequence set forth in SEQ ID NO: 1.

Another embodiment of the present invention comprises a composition to inhibit the growth or proliferation of cancer cells in an individual comprising a pharmaceutically effective amount of a compound which provides sufficient angiotensin-(1-7) receptor agonist to inhibit growth or proliferation of the cancer cells.

In one embodiment, the present invention comprises a method to inhibit cell growth or proliferation comprising application an agonist for the angiotensin-(1-7) receptor to the cells, wherein the cells have a functional angiotensin-(1-7) receptor.

In another embodiment, the present invention comprises a method to inhibit the growth or proliferation of cancer cells in an individual comprising application of a pharmaceutically effective amount of an agonist for the angiotensin-(1-7) receptor to the individual, wherein a pharmaceutically effective amount comprises sufficient angiotensin-(1-7) receptor agonist to inhibit growth or proliferation of the cancer cells.

In yet another embodiment, the present invention comprises a method to inhibit the growth or proliferation of cancer cells in an individual comprising application of a pharmaceutically effective amount of a compound which increases the efficacy or amount of circulating or cellular angiotensin-(1-7) receptor agonist.

In yet another embodiment, the present invention comprises a kit for inhibiting cancer cell growth and proliferation in an individual comprising: (a) at least one container comprising a pharmaceutically effective amount of a functional agonist for the angiotensin-(1-7) receptor; (b) a pharmaceutically acceptable carrier; and (c) instructions for use.

From the foregoing summary, it is apparent that an object of the present invention is to provide methods and compositions for the use of angiotensin-(1-7) receptor agonists as anti-cancer therapeutics. There are, of course, additional features of the invention which will be described hereinafter and which will form the subject matter of the claims appended hereto. It is to be understood that the invention is not limited in its application to the specific details as set forth in the following description and figures. The invention is capable of other embodiments and of being practiced or carried out in various ways.

DETAILED DESCRIPTION OF THE INVENTION

Figure 1:
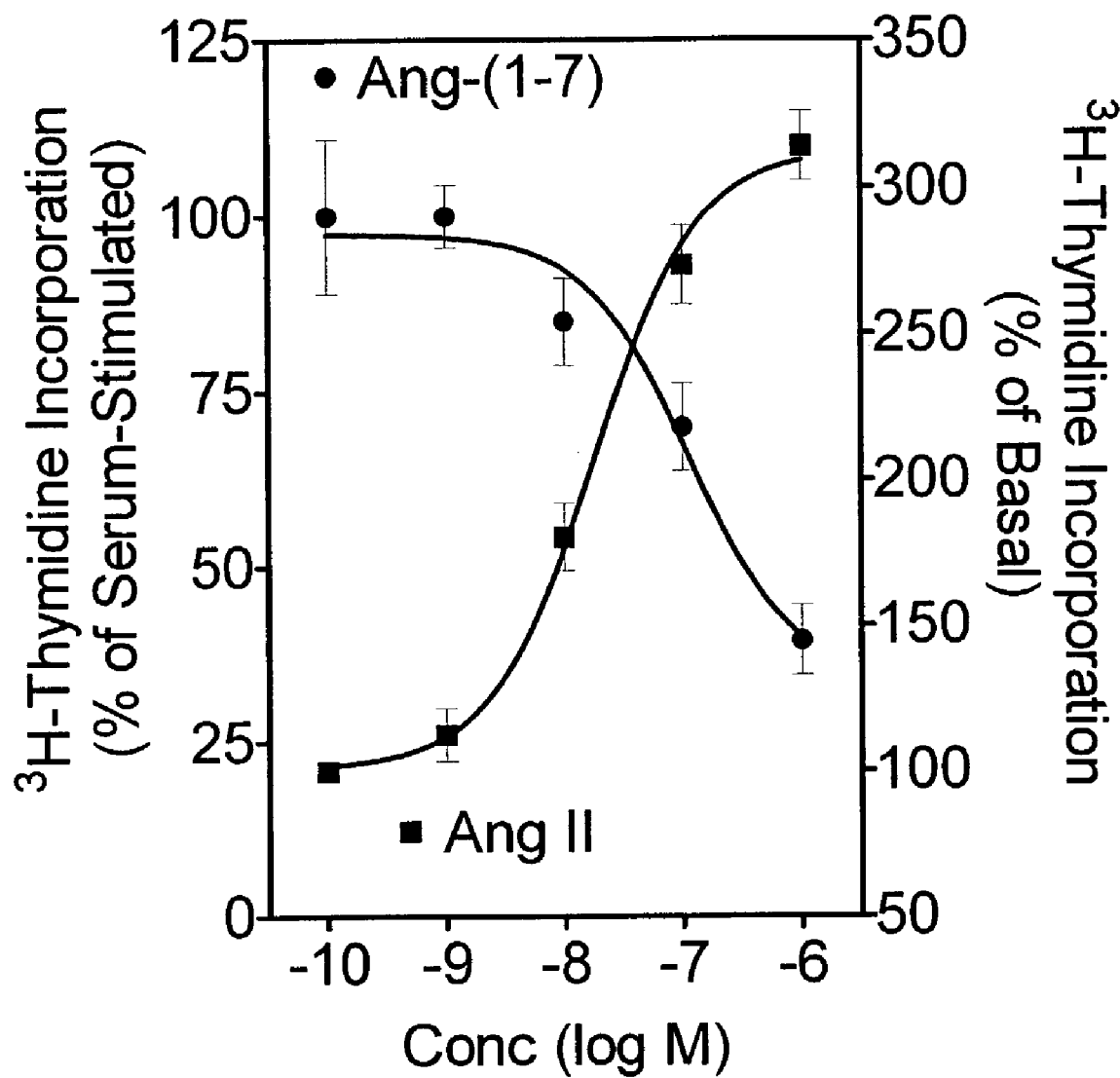
FIG. 1 shows the dose-dependent effect of angiotensin peptides on 3H-thymidine incorporation into vascular smooth muscle cells (VSMCs) in accordance with an embodiment of the present invention.

The present invention describes the use of angiotensin-(1-7) receptor agonists, such as angiotensin-(1-7) [Ang-(1-

7)] (Asp-Arg-Val-Tyr-Ile-His-Pro) (SEQ ID NO: 1) as anticancer therapeutics. Thus, embodiments of the present invention recognize that agonists of the Ang-(1-7) receptor can inhibit tumor cell growth in vitro and in vivo.

In one embodiment, the present invention comprises a method to inhibit cell growth or proliferation comprising application of an agonist for the angiotensin-(1-7) receptor to the cells wherein the cells have a functional angiotensin-(1-7) receptor.

The receptor may be located in either the membrane or within the cellular compartments. Preferably, the cells comprise cancer cells. More preferably, the cancer comprises bladder cancer, breast cancer, brain cancer, colon cancer, endometrial cancer, head and neck cancer, leukemia, lymphoma, lung cancer, melanoma, liver cancer, rectal cancer, ovarian cancer, prostate cancer, renal cancer, bone cancer, pancreatic cancer or skin cancer.

In an embodiment, the angiotensin-(1-7) receptor agonist comprises angiotensin-(1-7) peptide having the sequence set forth in SEQ ID NO: 1. In an embodiment, the angiotensin-(1-7) receptor agonist is modified to increase its chemical stability in vivo. In an alternate embodiment, the angiotensin-(1-7) receptor agonist comprises a fragment of angiotensin-(1-7) or a functional equivalent of angiotensin-(1-7) comprising conservative amino acid substitutions, wherein conservative amino acid substitutions are those substitutions which do not significantly effect the structure or function of the peptide. In yet another embodiment, the angiotensin-(1-7) receptor agonist comprises a non-peptide agonist.

In yet another embodiment, the present invention comprises a method to inhibit the growth or proliferation of cancer cells in an individual comprising application of a pharmaceutically effective amount of an agonist for the angiotensin-(1-7) receptor to the individual, wherein a pharmaceutically effective amount comprises sufficient angiotensin-(1-7) receptor agonist to inhibit growth or proliferation of the cancer cells. Preferably, the individual is human.

Preferably, the cancer comprises cells having a functional angiotensin-(1-7) receptor. The receptor may be on the cell membrane or intracellular. Also preferably, the cancer comprises bladder cancer, breast cancer, brain cancer, colon cancer, endometrial cancer, head and neck cancer, leukemia, lymphoma, lung cancer, melanoma, liver cancer, rectal cancer, ovarian cancer, prostate cancer, bone cancer, pancreatic cancer, skin cancer, or renal cancer.

In an embodiment, the angiotensin-(1-7) receptor agonist comprises angiotensin-(1-7) peptide having the sequence set forth in SEQ ID NO: 1. In an embodiment, the angiotensin-(1-7) receptor agonist is modified to increase its chemical stability in vivo. In an alternate embodiment, angiotensin-(1-7) receptor agonist comprises a fragment of angiotensin-(1-7) or a functional equivalent of angiotensin-(1-7) comprising conservative amino acid substitutions, wherein conservative amino acid substitutions are those substitutions which do not significantly effect the structure or function of the peptide. In yet another embodiment, the angiotensin-(1-7) receptor agonist comprises a non-peptide agonist.

Also preferably, the method includes application of a compound which increases the efficacy or amount of circulating or cellular angiotensin-(1-7) agonist. For example, in an embodiment, the method includes application of a compound that increases angiotensin-(1-7) synthesis. Alternatively, the method includes application of a compound that decreases angiotensin-(1-7) agonist degradation. In an embodiment, the method includes application of a compound that is an antagonist of other, non-angiotensin-(1-7) receptor subtypes, such as an anatagonist for the $AT_1$ angiotensin receptor.

Also preferably, application of a pharmaceutically effective amount of angiotensin-(1-7) receptor agonist in the individual increases cellular prostacyclins. Also preferably, application of a pharmaceutically effective amount of angiotensin-(1-7) receptor agonist in the individual increases cellular cAMP.

In an embodiment, application of a pharmaceutically effective amount of angiotensin-(1-7) receptor agonist increases the expression of genes involved in tumor suppression, apoptosis, and/or cell cycle inhibition in the cancer cells. Preferably, the genes showing increased expression comprise BAD, oncostatin M-specific beta subunit, PDCD2, EGF response factor 1, CASP4, RBQ-3, p16-INK, menin, checkpoint suppressor 1, BAK, apoptotic protease activating factor-1, SOCS-3, insulin-like growth factor binding protein 2, B-myb or the fau tumor suppressor.

Alternatively, or additionally, application of a pharmaceutically effective amount of angiotensin-(1-7) receptor agonist in the individual may also decrease the levels of known oncogenes, protein kinases, and/or cell cycle progression genes in the cancer cells. Preferably, the genes showing decreased expression comprise cell cycle entry regulator, ERK1, cell cycle progression 2 protein, p21/K-ras 2B oncogene, epithelial cell kinase, ser/thr kinase, MAP kinase kinase 5 (MEK5), beta catenin, tyrosine-protein kinase receptor tyro3 precursor, protein phosphatase 2A B56-alpha, cyclin-dependent kinase regulatory subunit (CDC28), cell division protein kinase 6 (CDK6), c-myc oncogene, ERBB-3 receptor protein tyrosine kinase, A-kinase anchoring protein, or rho C.

In an embodiment, there is a discrete dosage range of angiotensin-(1-7) receptor agonist which is effective in inhibiting tumor cell growth. Preferably, the dose of angiotensin-(1-7) receptor agonist results in a local concentration of angiotensin-(1-7) receptor agonist at the cancer which ranges from 0.005 nM to 10 μM. More preferably, the dose of angiotensin-(1-7) receptor agonist results in a local concentration of angiotensin-(1-7) receptor agonist at the cancer which ranges from 0.05 nM to 1 μM. Even more preferably, the dose of angiotensin-(1-7) receptor agonist results in a local concentration of angiotensin-(1-7) or angiotensin-(1-7) receptor agonist at the cancer which ranges from 1 nM to 100 nM.

In yet another aspect, the present invention comprises a method to inhibit the growth or proliferation of cancer cells in an individual comprising application of a pharmaceutically effective amount of a compound to the individual which increases the efficacy or amount of circulating or cellular angiotensin-(1-7) agonist.

In an embodiment, the compound which increases the efficacy or amount of cellular angiotensin-(1-7) agonist increases angiotensin-(1-7) synthesis. In another embodiment, the compound which increases the efficacy or amount of cellular angiotensin-(1-7) agonist may decrease angiotensin-(1-7) agonist degradation, metabolism or clearance. In yet another embodiment, the compound which increases the efficacy or amount of cellular angiotensin-(1-7) agonist comprises an angiotensin $AT_1$ receptor antagonist. Preferably, the cancer treated by the method of the present invention comprises bladder cancer, breast cancer, brain cancer, colon cancer, endometrial cancer, head and neck cancer, leukemia, lymphoma, lung cancer, melanoma, liver cancer, rectal cancer, ovarian cancer, prostate cancer, bone cancer, pancreatic cancer, skin cancer, or renal cancer.

In another aspect, the present invention comprises a composition for inhibition of cell growth or proliferation comprising a pharmaceutically effective amount of an agonist for the angiotensin-(1-7) receptor in a pharmaceutically acceptable carrier, wherein a pharmaceutically effective amount of angiotensin-(1-7) receptor agonist comprises an amount which is sufficient to inhibit cell growth or proliferation. Preferably, the cells comprise cancer cells. More preferably, the cancer comprises bladder cancer, breast cancer, brain cancer, colon cancer, endometrial cancer, head and neck cancer, leukemia, lymphoma, lung cancer, melanoma, liver cancer, rectal cancer, ovarian cancer, prostate cancer, renal cancer, bone cancer, pancreatic cancer or skin cancer.

In another aspect, the present invention comprises a composition for inhibition of cancer cell growth or proliferation comprising a pharmaceutically effective amount of an agonist for the angiotensin-(1-7) receptor in a pharmaceutically acceptable carrier, wherein a pharmaceutically effective amount of angiotensin-(1-7) receptor agonist comprises an amount which is sufficient to inhibit cancer cell growth and/or proliferation.

Preferably, the cancer comprises cells having a functional angiotensin-(1-7) receptor. The receptor may be located on the cell membrane or intracellular. For example, the cancer may comprise cells whose functional angiotensin-(1-7) receptor signals or secretes a chemical or protein that inhibits cancer cell growth. Also, in an embodiment, the cancer is in a human subject. Also preferably, the cancer comprises bladder cancer, breast cancer, brain cancer, colon cancer, endometrial cancer, head and neck cancer, leukemia, lymphoma, lung cancer, melanoma, liver cancer, rectal cancer, ovarian cancer, prostate cancer, renal cancer, bone cancer, pancreatic cancer, or skin cancer.

In an embodiment, the angiotensin-(1-7) receptor agonist of the composition comprises angiotensin-(1-7) peptide having the sequence set forth in SEQ ID NO: 1. In an embodiment, the angiotensin-(1-7) receptor agonist of the composition is modified to increase its chemical stability in vivo. In an alternate embodiment, the angiotensin-(1-7) receptor agonist comprises a fragment of angiotensin-(1-7) or a functional equivalent of angiotensin-(1-7) comprising conservative amino acid substitutions, wherein conservative amino acid substitutions are those substitutions which do not significantly effect the structure or function of the peptide. In yet another embodiment, the angiotensin-(1-7) receptor agonist comprises a non-peptide agonist.

Also preferably, the composition includes a compound which increases the efficacy or amount of circulating or cellular angiotensin-(1-7) agonist. In an embodiment, the compound which increases the efficacy or amount of angiotensin-(1-7) agonist increases angiotensin-(1-7) synthesis. In another embodiment, the compound which increases the efficacy or amount of angiotensin-(1-7) agonist may decrease angiotensin-(1-7) degradation, metabolism or clearance. In yet another embodiment, the compound which increases the efficacy or amount of angiotensin-(1-7) agonist comprises a non-Ang-(1-7) angiotensin receptor antagonist, such an antagonist of the $AT_1$ angiotensin receptor.

In an embodiment, a pharmaceutically effective amount of angiotensin-(1-7) receptor agonist increases cellular prostacyclins. In an embodiment, a pharmaceutically effective amount of angiotensin-(1-7) receptor agonist increases cellular cAMP.

Also, in an embodiment, a pharmaceutically effective amount of angiotensin-(1-7) receptor agonist increases the expression of genes involved in tumor suppression, apoptosis, and/or cell cycle inhibition. Preferably, the genes showing increased expression comprise BAD, oncostatin M-specific beta subunit, PDCD2, EGF response factor 1, CASP4, RBQ-3, p16-INK, menin, checkpoint suppressor 1, BAK, apoptotic protease activating factor-1, SOCS-3, insulin-like growth factor binding protein 2, B-myb or the fau tumor suppressor.

Alternatively, or additionally, a pharmaceutically effective amount of angiotensin-(1-7) receptor agonist may decrease the levels of known oncogenes, protein kinases, and/or cell cycle progression genes in the cancer. Preferably, the genes showing decreased expression comprise cell cycle entry regulator, ERK1, cell cycle progression 2 protein, p21/K-ras 2B oncogene, epithelial cell kinase, ser/thr kinase, MAP kinase kinase 5 (MEK5), beta catenin, tyrosine-protein kinase receptor tyro3 precursor, protein phosphatase 2A B56-alpha, cyclin-dependent kinase regulatory subunit (CDC28), cell division protein kinase 6 (CDK6), c-myc oncogene, ERBB-3 receptor protein tyrosine kinase, A-kinase anchoring protein, or rho C.

In an embodiment, there is a discrete dosage range of angiotensin-(1-7) receptor agonist which is effective in inhibiting tumor cell growth. Preferably, the dose of angiotensin-(1-7) receptor agonist results in a local concentration of angiotensin-(1-7) receptor agonist at the cancer which ranges from 0.005 nM to 10 μM. More preferably, the dose of angiotensin-(1-7) receptor agonist results in a local concentration of angiotensin-(1-7) receptor agonist at the cancer which ranges from 0.05 nM to 1 μM. Even more preferably, the dose of angiotensin-(1-7) receptor agonist results in a local concentration of angiotensin-(1-7) receptor agonist at the cancer which ranges from 1 nM to 100 nM.

In another aspect, the present invention comprises a composition to inhibit the growth of cancer cells in an individual comprising a pharmaceutically effective amount of a compound which increases the efficacy or amount of circulating or cellular angiotensin-(1-7) agonist in a pharmaceutical carrier, wherein a pharmaceutically effective amount provides endogenous levels of angiotensin-(1-7) receptor agonist which is sufficient to inhibit cancer cell growth or proliferation. For example, in an embodiment, the method includes application of a compound that increases angiotensin-(1-7) synthesis. In another embodiment, the compound which increases the efficacy or amount of cellular angiotensin-(1-7) agonist may decrease angiotensin-(1-7) agonist degradation, metabolism or clearance. In yet another embodiment, the compound which increases the efficacy or amount of cellular angiotensin-(1-7) agonist comprises a non-Ang-(1-7) angiotensin receptor antagonist, such as an antagonist of the $AT_1$ angiotensin receptor.

For example, such compounds may include ACE inhibitors, or any pharmaceutical that blocks either the $AT_1$ angiotensin II receptor. Such compounds act to cause an increase in Ang-(1-7) and thereby, can contribute to Ang-(1-7) mediated inhibition of cancer growth. In an embodiment, the compounds comprise angiotensin receptor blockers.

Preferably, the cancer treated by the method of the present invention comprises bladder cancer, breast cancer, brain cancer, colon cancer, endometrial cancer, head and neck cancer, leukemia, lymphoma, lung cancer, melanoma, liver cancer, rectal cancer, ovarian cancer, prostate cancer, bone cancer, pancreatic cancer, skin cancer, or renal cancer.

In yet another aspect, the present invention comprises a kit for inhibiting cancer cell growth in an individual comprising: (a) at least one container comprising a pharmaceutically effective amount of a functional agonist for the angiotensin-(1-7) receptor, wherein a pharmaceutically effective amount comprises an amount of angiotensin-(1-7) receptor agonist which is sufficient to inhibit cancer cell growth or proliferation; (b) a pharmaceutically acceptable carrier; and (c) instructions for use.

Preferably, the cancer cells comprise a functional angiotensin-(1-7) receptor. The receptor may be located on the cell membrane, or intracellular. In an embodiment, the cancer comprises bladder cancer, breast cancer, brain cancer, colon cancer, endometrial cancer, head and neck cancer, leukemia, lymphoma, lung cancer, melanoma, liver cancer, rectal cancer, ovarian cancer, prostate cancer, bone cancer, pancreatic cancer, skin cancer, or renal cancer.

In an embodiment, the angiotensin-(1-7) receptor agonist comprises angiotensin-(1-7) peptide having the sequence set forth in SEQ ID NO: 1. Preferably, the angiotensin-(1-7) receptor agonist used in the kit is modified to increase its chemical stability in vivo. In an embodiment, the angiotensin-(1-7) receptor agonist comprises a fragment of angiotensin-(1-7) or a functional equivalent of angiotensin-(1-7) comprising conservative amino acid substitutions. Alternatively, the angiotensin-(1-7) receptor agonist, may comprise a non-peptide agonist.

Also preferably, the kit includes a compound which increases the efficacy or amount of cellular angiotensin-(1-7) agonist in the cells. In an embodiment, the compound which increases the efficacy or amount of cellular angiotensin-(1-7) increases angiotensin-(1-7) synthesis. In another embodiment, the compound which increases the efficacy or amount of cellular angiotensin-(1-7) agonist may decrease angiotensin-(1-7) agonist degradation, metabolism or clearance. In yet another embodiment, the compound which increases the efficacy or amount of cellular angiotensin-(1-7) agonist comprises a non-Ang-(1-7) angiotensin receptor antagonist, such as an antagonist of the $AT_1$ angiotensin receptor.

Angiotensin-(1-7) is a Physiological Mediator of Cell Growth

Studies indicate that the angiotensin peptides may be associated with a variety of cellular activities. Still, angiotensin-(1-7) has long been considered an inactive product of AngII degradation. Only a few studies have implicated angiotensin peptides as potentially having a role in the regulation of cell growth and/or cancer. For example, in two studies, patients receiving ACE inhibitors were found to have reduced relative risk (0.73 and 0.79) of cancer (Jick, H. et al., *Lancet,* 1997, 349:525-528;and Pahor, M. et al., *Am. J. Hypertens.,* 1996, 9:695-699). These reductions in risk were not, however, statistically significant. In a retrospective study of 5207 patients in Scotland, the relative risks of incident and fatal cancer among the 1559 patients treated with ACE inhibitors were reduced, to 0.72 and 0.65, respectively, with the relative risk lowest in patients with lung or sex-specific cancer (Lever, A. F. et al., *Lancet,* 1998, 352: 179-184). Other studies suggested that treatment with ACE inhibitors may attenuate the growth of preneoplastic liver cells (Volpert, J. J. et al., *J. Clin. Invest.,* 1996, 98:671-679) and renal cell carcinoma (Hii, S. I. et al., *British Journal of Cancer,* 1998, 77:880-883). While these studies suggest a role for ACE inhibitors in reducing cancer risk, there is no indication as to the mechanism by which a lower risk of cancer may have occurred, or that Ang-(1-7) played a role.

The present invention describes the use of angiotensin-(1-7) [Ang-(1-7)] peptide and other Ang-(1-7) receptor agonists to inhibit cancer growth. Thus, in an embodiment, the present invention recognizes that Ang-(1-7) peptide (Asp-Arg-Val-Tyr-Ile-His-Pro) (SEQ ID NO: 1) binds to a specific receptor present on tumor cells to affect second messengers associated with regulation of cell growth and proliferation. In an embodiment, the present invention describes that Ang-(1-7) binds to specific receptors to invoke a decrease in the expression of genes associated with cell growth and proliferation and to invoke an increase in expression of genes associated with suppression of cell proliferation and/or apoptosis and cell death.

Thus, in one embodiment, the present invention comprises a method to inhibit cell proliferation comprising application of angiotensin-(1-7) [Ang-(1-7)] or other agonists for the angiotensin-(1-7) receptor to the cells of interest. In another embodiment, the present invention comprises a method to inhibit cell proliferation comprising application of a compound which increases the efficacy or amount of cellular angiotensin-(1-7) to cells comprising the Ang-(1-7) receptor. For example, and referring now to FIGS. 1-4, angiotensin-(1-7) inhibits vascular smooth muscle cell (VSMC) growth both in vitro (FIGS. 1 and 2), and in vivo (FIGS. 3 and 4), suggesting that Ang-(1-7) may act as an endogenous regulator of cell growth.

Figure 2:
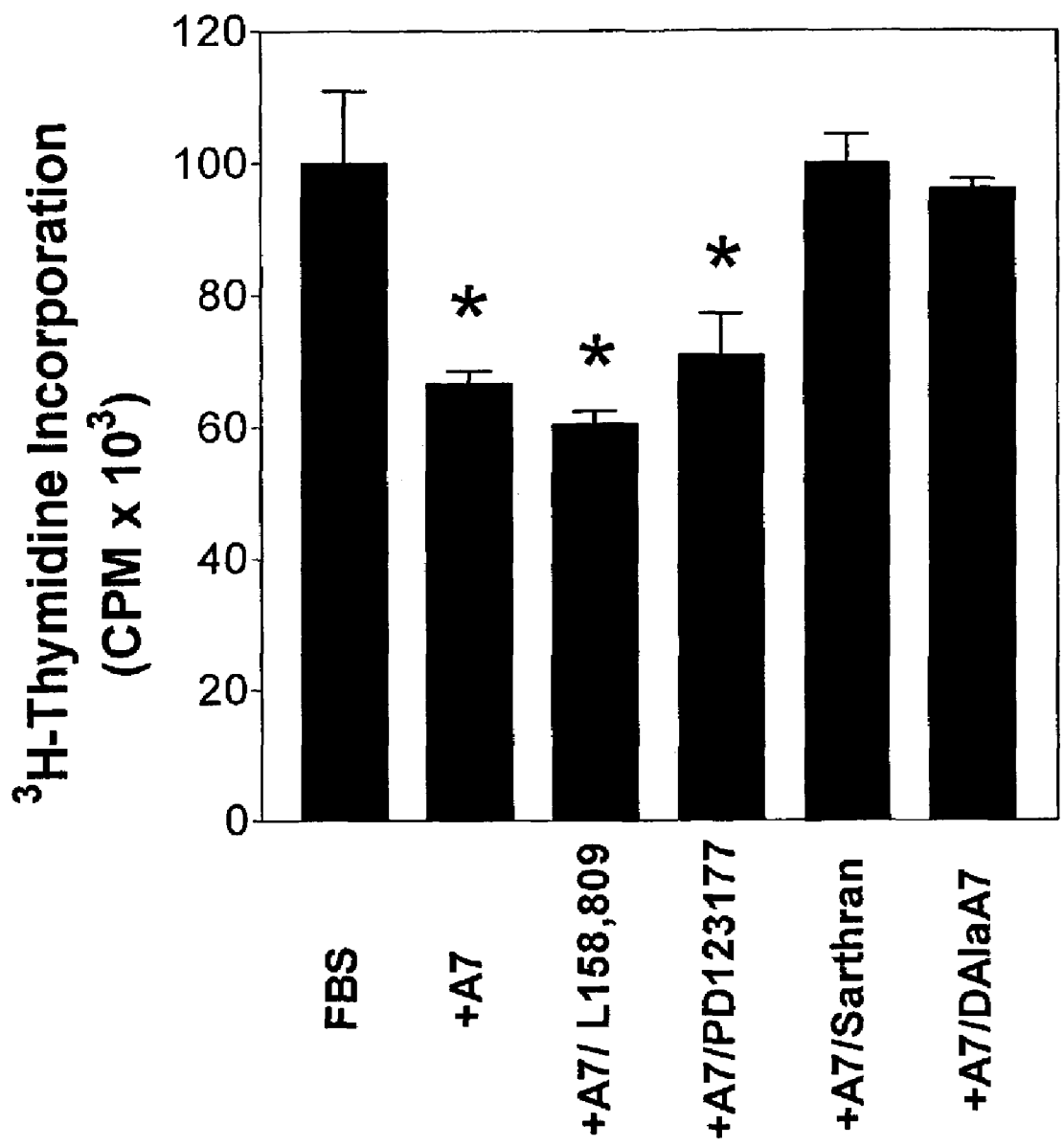
FIG. 2 shows inhibition of the 1 µM Ang-(1-7) (Asp-Arg-Val-Tyr-Ile-His-Pro) (SEQ ID NO: 1) mediated reduction (+A7) in serum-stimulated growth (FBS) by [Sar$^1$-Thr$^8$]-Ang II (Sarthran) (Sar-Arg-Val-Tyr-Ile-His-Pro-Thr) (SEQ ID NO: 2) or [D-Ala$^7$]-Ang-(1-7) (DAlaA7) (Asp-Arg-Val-Tyr-Ile-His-[D]Ala) (SEQ ID NO: 3) but not by AT$_1$ (L158, 809) or AT$_2$ (PD123177) receptor antagonists in accordance with an embodiment of the present invention.

Thus, FIG. 1 shows the dose-dependent effect of angiotensin peptides on 3H-thymidine incorporation into vascular smooth muscle cells (VSMCs). It can be seen that Ang-(1-7) inhibits thymidine incorporation into DNA in a dose-dependent manner with an effective concentration for 50% inhibition (IC50) of about 115 nM. FIG. 2 shows that the ability of Ang-(1-7) to inhibit thymidine uptake is receptor mediated. Thus, as shown in FIG. 2, the 1 µM Ang-(1-7)-mediated reduction (+A7) in serum-stimulated growth (FBS) is inhibited by [$Sar^1$-$Thr^8$]-Ang II (Sarthran) or [D-$Ala^7$]-Ang-(1-7) (DalaA7) (which bind to the Ang-(1-7) receptor) but not by $AT_1$ (L158,809) or $AT_2$ (PD123177) receptor antagonists.

Figure 3:
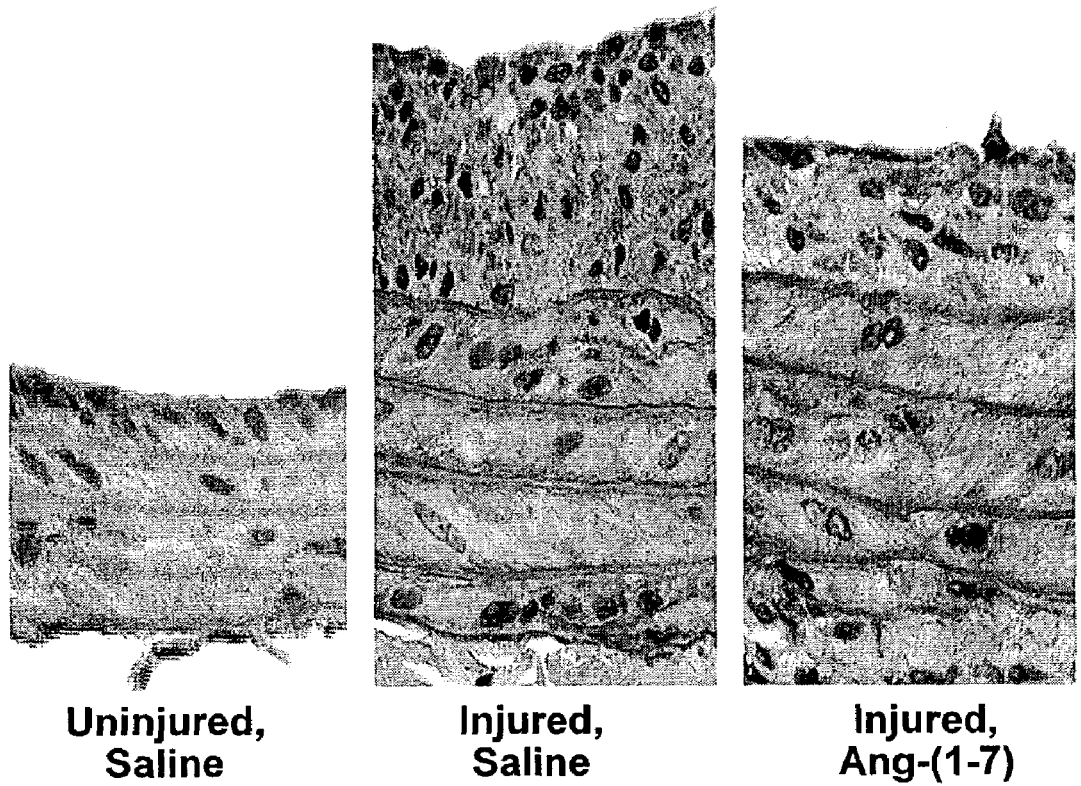
FIG. 3 shows stained sections of: an uninjured rat carotid artery; a saline-treated injured carotid artery; and an injured carotid artery treated with Ang-(1-7), in accordance with an embodiment of the present invention.
Figure 4:
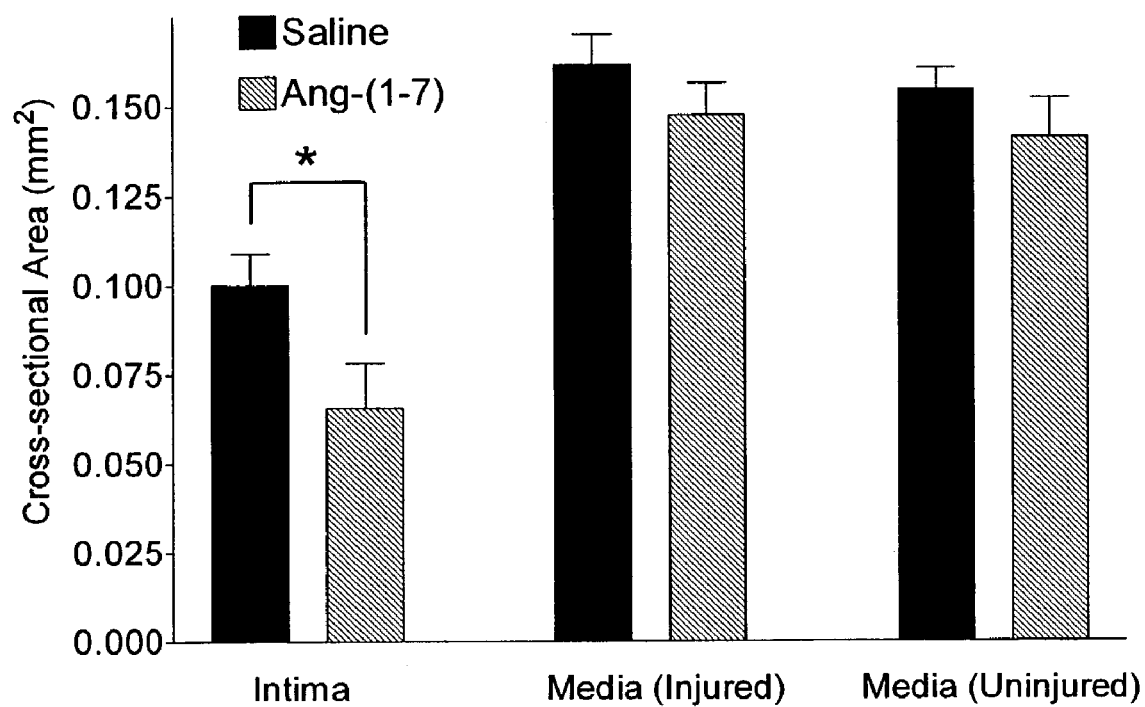
FIG. 4 shows morphometric analysis of intima and media of injured rat carotid arteries and the media of uninjured rat carotid arteries in balloon catheter-injured rats infused with either saline or Ang-(1-7) (*P<0.05; n=8) in accordance with an embodiment of the present invention.

FIG. 3 shows stained sections of an uninjured rat carotid artery, a saline-treated injured carotid artery, and an injured corotid artery treated with Ang-(1-7). Thus, in an embodiment, Ang-(1-7) reverses the cellular proliferation seen upon vascular injury. Morphometric analysis of carotid artery cross-sections indicates that Ang-(1-7) infusion significantly reduces the neointimal area compared to rats infused with saline but has no effect on the medial area of the injured or the contralateral uninjured artery as compared to saline controls (FIGS. 3 and 4). Thus, Ang-(1-7) inhibits vascular growth in vivo and may prevent vascular re-stenosis mediated by the proliferative response of smooth muscle cells in blood vessels. For example, vascular re-stenosis is a complication seen when vascular stents are used to prevent vessel occlusion in response to angioplasty and similar procedures.

The Effects of Ang-(1-7) Are Mediated by a Specific Receptor

In an embodiment, the effect of Ang-(1-7) on cell growth and/or proliferation is receptor mediated. Ang-(1-7) is a poor competitor at the prototypical $AT_1$ angiotensin receptor in VSMC (Jaiswal, N. et al., *Hypertension,* 1993, 21:900-905; and Jaiswal, N. et al., *J. Pharmacol. Exp. Ther.,* 1993, 265:664-673) or the $AT_2$ angiotensin receptor (Chappell, M. C. et al., *Peptides,* 1995, 16:741-747;and Tallant, E. A. et al., *Hypertension,* 1991, 17:1135-1143). Thus, Ang-(1-7) displays $IC_{50}$ levels in the micromolar range at the $AT_1$ or $AT_2$ angiotensin receptor (Tallant, E. A. et al., *Hypertension,* 1999, 34:950-957).

As described herein, $IC_{50}$ is the concentration of an agent which provides 50% of the total inhibition detected for a biological effect of interest, as for example, 50% inhibition of receptor binding or 50% inhibition of $^3$H-thymidine uptake.

Angiotensin receptors are pharmacologically defined by their selectivity for the prototypical ligand losartan and similar antagonists such as L-1 58,809, while AT$_2$ receptors show selectivity for the antagonist PD 123177 or PD 123319 (de Gasparo et al., 1995). Ang II, by stimulation of AT$_1$ receptors, is a potent vasoconstrictor and stimulates thirst and aldosterone release. Inhibition of its production or effect using ACE inhibitors or AT$_1$ receptor antagonists reduces mean arterial pressure (Tallant, E. A. and Ferrario, C. M. *Exp. Opin. Invest. Drugs* 1996, 5:1201-1214). In contrast, activation of AT$_2$ receptors by Ang II is associated with vasodilation and reduced cell growth (Carey R. M. et al., *Am. J. Hypertens.* 2001, 6:98-1-2).

[D-Ala$^7$]-Ang-(1-7), a modified form of Ang-(1-7), selectively blocks responses to Ang-(1-7). [D-Ala$^7$]-Ang-(1-7) is a poor competitor at the AT$_1$ or AT$_2$ receptor, and does not block pressor or contractile responses to Ang II (Britto, R. R. et al., *Hypertension*, 1997, 30:549-556; Fontes, M. A. P. et al., (*Brain Res.*, 1994, 665:175-180Oliveira, D. R. et al., *Hypertension*, 27:1998, 1284-1290;and Santos, R. A. S. et al., *Brain Res. Bull.*, 1994, 35:293-298). Thus, an Ang-(1-7) binding site on bovine aortic endothelial cells [BAEC] which was competed for by [Sar$^1$-Ile$^8$]-AngII and [D-Ala$^7$]-Ang-(1-7) but not by losartan or PD123319 has been identified (Tallant, E. A. et al., *Hypertension*, 1996, 29:388-393; and Heitsch, H. et al., *Hypertension*, 2001, 37:72-76). A similar $^{125}$I-Ang-(1-7) binding site, sensitive to Ang-(1-7) and [D-Ala$^7$]-Ang-(1-7), found in the endothelium of canine coronary artery rings (Ferrario, C. M. et al., *Hypertension*, 1997, 30:535-541), consistent with functional effects of Ang-(1-7) in canine and porcine coronary arteries (Brosnihan, K. R. and Ferrario, C. M., *Hypertension*, 1996, 27:523-528;and Porsti, I. et al., *Br. J. Pharmacol.*, 1994, 111:652-654). As described herein, a similar binding site for Ang-(1-7) has been identified on VSMCs (Iyer, S.N., et al., J. Cardiovasc. Pharmacol., 2000, 36:109-117).

Thus, there is a specific angiotensin-(1-7) [Ang-(1-7)] receptor, that is sensitive to [Sar$^1$-Thr$^8$]-Ang II or [D-Ala$^7$]-Ang-(1-7) but not to losartan or PD123319. In an embodiment, the action of Ang-(1-7) to inhibit cell growth and/or cell proliferation comprises an interaction with a specific receptor for Ang-(1-7). As described herein, this angiotensin-(1-7) receptor may be referred to as the AT$_{(1-7)}$ receptor, in accordance with the guidelines established by the International Union of Pharmacology Nomenclature Subcommittee for Angiotensin Receptors (Bumpus, F. M. et al., *Hypertension*, 1991, 17:720-721;and De Gasparo, M. et al., *Hypertension*, 1995, 25:924-927). The AT$_{(1-7)}$ receptor (or Ang-(1-7) receptor) is defined by its sensitivity to Ang-(1-7), its antagonism by [Sar$^1$-Thr$^8$]-Ang II and [D-Ala$^7$]-Ang-(1-7), and its lack of response to losartan or PD123319, either functionally, or in competition for binding.

For example, and referring again to FIG. 2, inhibition of mitogen-stimulated VSMC growth by Ang-(1-7) is not prevented by the AT$_1$ antagonist L158,809 or the AT$_2$ antagonist PD 123319. However, [Sar$^1$-Thr$^8$]-Ang II or the Ang-(1-7) antagonist [D-Ala$^7$]-Ang-(1-7) effectively blocks growth inhibition of VSMCs by Ang-(1-7). Also, in an embodiment, the inhibition of serum-stimulated growth in cancer cells is attenuated by the selective Ang-(1-7) antagonist [D-Ala$^7$]-Ang-(1-7), but not by an AT$_1$ or AT$_2$ receptor antagonists (see FIG. 7, and discussion below).

In an embodiment, agonists other than Ang-(1-7) for the Ang-(1-7) receptor may be used in the methods of the present invention. In yet another embodiment, non-peptide agonists such as those described in U.S. Pat. Nos. 6,429,222 and 6,235,766 (incorporated in their entireties by reference hererein) may be employed.

In an embodiment, the angiotensin-(1-7) or other angiotensin-(1-7) receptor agonist is chemically modified to increase its stability in vivo. For example, to increase stability, the peptide may be modified at several positions to protect against aminopeptidase and endopeptidase hydrolysis. For aminopeptidase protection, the amino (N) terminus of the peptide may be modified by substituting sarcosine for aspartic acid (Asp) or acetylated aspartic acid for aspartic acid. To protect against endopeptidase attack, primarily ACE hydrolysis which occurs at the Ile$^5$-His$^6$ bond of Ang-(1-7), D-isoleucine and D-histidine may be substituted for isoleucine at position 5 (Ile$^5$) and histidine at position 6 (His$^6$), respectively, of the peptide. Additionally, a reduced or methyline isostere bond may be introduced between Ile$^5$ and His$^6$.

In yet another embodiment, the angiotensin-(1-7) or angiotensin-(1-7) receptor agonist comprises a fragment of angiotensin-(1-7) or a functional equivalent of angiotensin-(1-7) having conservative amino acid substitutions, wherein conservative amino acid substitutions are defined to be those amino acid substitutions which do not affect the apparent structure, or inhibit the function, of the peptide.

Angiotensin-(1-7) Inhibits Cancer Cell Growth and Proliferation

In an embodiment, the present invention describes the use of agonists for the Ang-(1-7) receptor to inhibit growth and proliferation of cancer cells. Preferably, the Ang-(1-7) agonist may be used for inhibition of breast or lung cancer tumor growth (FIGS. 5-9). The inhibition of tumor growth by Ang-(1-7) seen in vitro (FIGS. 5-8) is also seen in vivo (FIG. 9) indicating that Ang-(1-7) is effective for tumor reduction in vivo.

Figure 5:
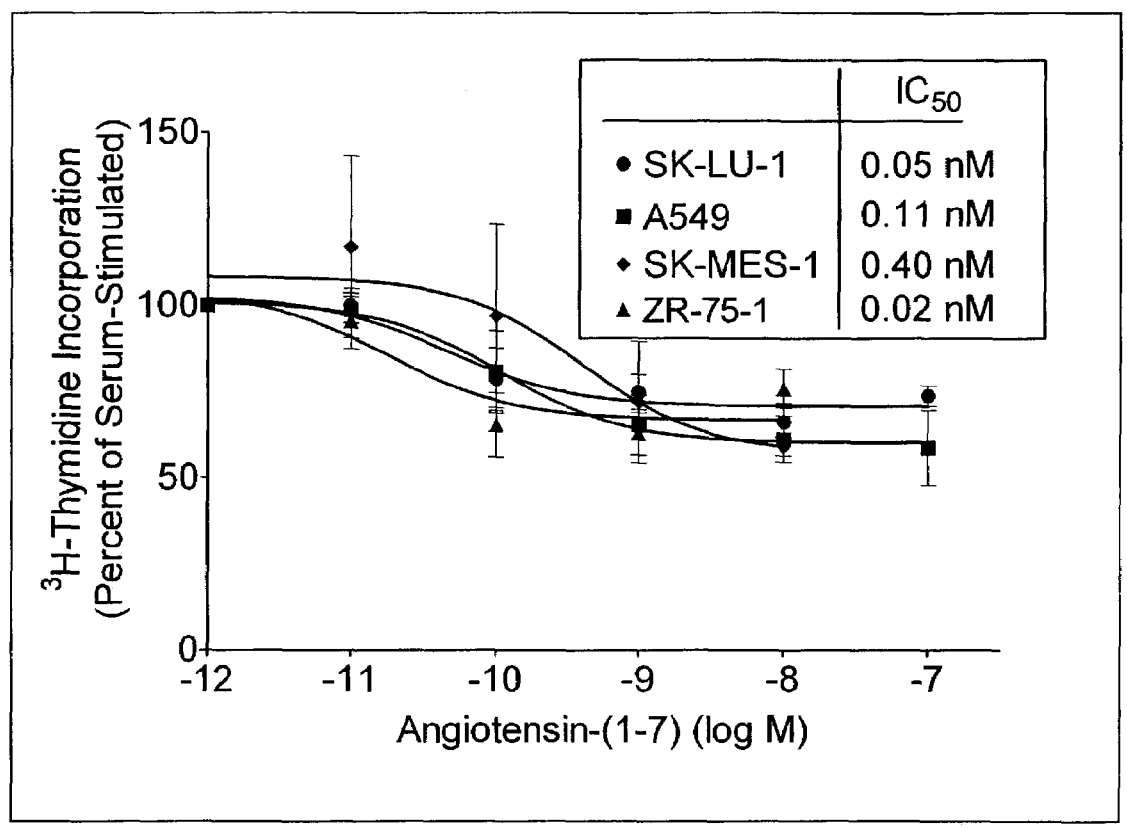
FIG. 5 shows that Ang-(1-7) causes a dose-dependent reduction in serum-stimulated $^3$H-thymidine incorporation into SK-LU-1, A549, and SK-MES-1 human lung cancer cells and ZR-75-1 human breast cancer cells (n=4-8, in triplicate) in accordance with an embodiment of the present invention.

Thus, Ang-(1-7) inhibits growth of human lung cancer cells (SK-LU-1, A549, SK-MES-1) and breast cancer cells (ZR-75-1), in a dose-dependent manner (FIG. 5). In an embodiment, the dose of Ang-(1-7) required for inhibition of cancer cells comprises levels of angiotensin-(1-7) used pharmacologically in animals or humans. Also preferably, the dose of angiotensin-(1-7) receptor agonist results in a local concentration of angiotensin-(1-7) agonist at the tumor which ranges from 0.0005 nM to 10 µM, and more preferably, from 0.05 nM to 1 µM, or even more preferably, from 1 nM to 100 nM (FIG. 5).

Thus, as shown in FIG. 5, Ang-(1-7) reduced tumor cell growth with an IC$_{50}$ of 0.05 nM for SK-LU-1 lung cancer cells, an IC$_{50}$ of 0.11 nM for A549 lung cancer cells, an IC$_{50}$ of 0.4 nM for SK-MES-1 lung cancer cells, and an IC$_{50}$ of 0.02 nM for ZR-75-1 breast cancer cells These concentrations of Ang-(1-7) are well within the range of Ang-(1-7) doses used pharmacologically in animals or humans.

Figure 6:
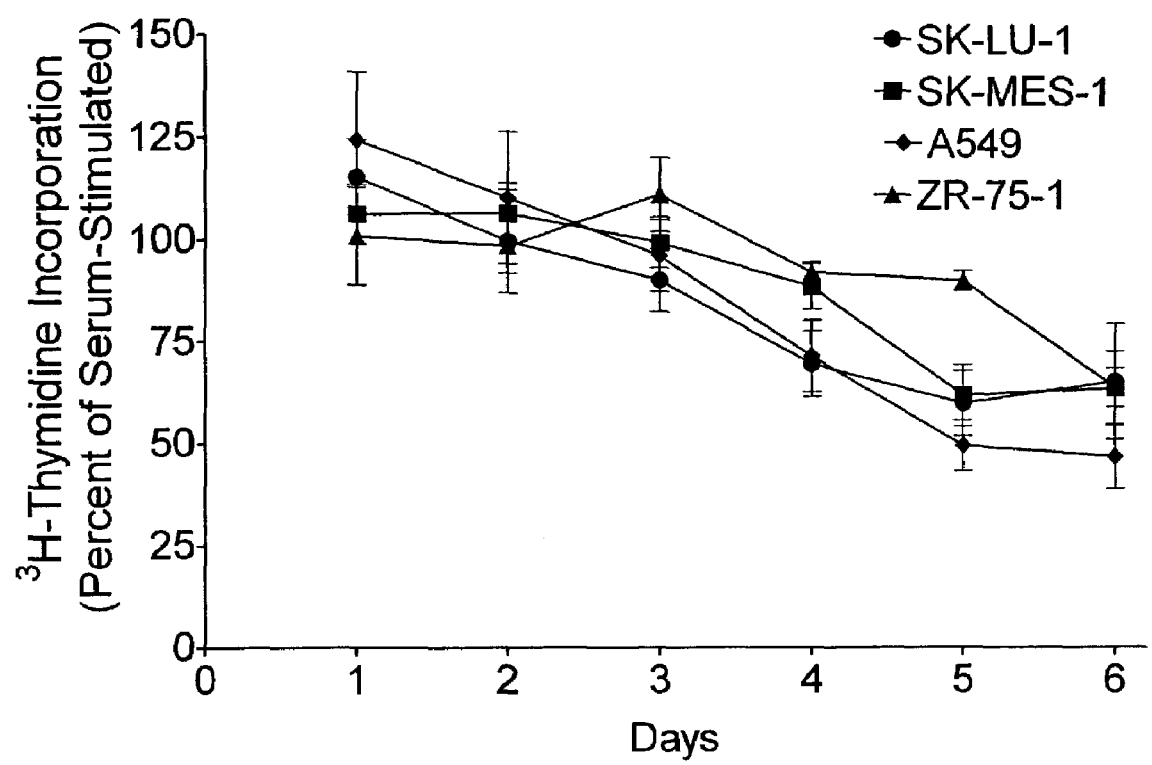
FIG. 6 shows a time-dependent reduction in $^3$H-thymidine incorporation into SK-LU-1, A549, and SK-MES-1 lung cancer cells and ZR-75-1 breast cancer cells in the presence of 100 nM Ang-(1-7) (n=3-4, in triplicate) in accordance with an embodiment of the present invention.

In an embodiment, the ability of Ang-(1-7) to inhibit tumor growth is a function of cell division and the length of the cell cycle. For example, the incorporation of $^3$H-thymidine into SK-LU-1, A549, and SK-MES-1 lung cancer cells and ZR-75-1 breast cancer cells stimulated to grow by the inclusion of 1% FBS is progressively reduced by daily addition of 100 nM Ang-(1-7) (FIG. 6). Thus, application of Ang-(1-7) may be hourly, daily, or over the course of weeks (FIG. 6).

Figure 7:
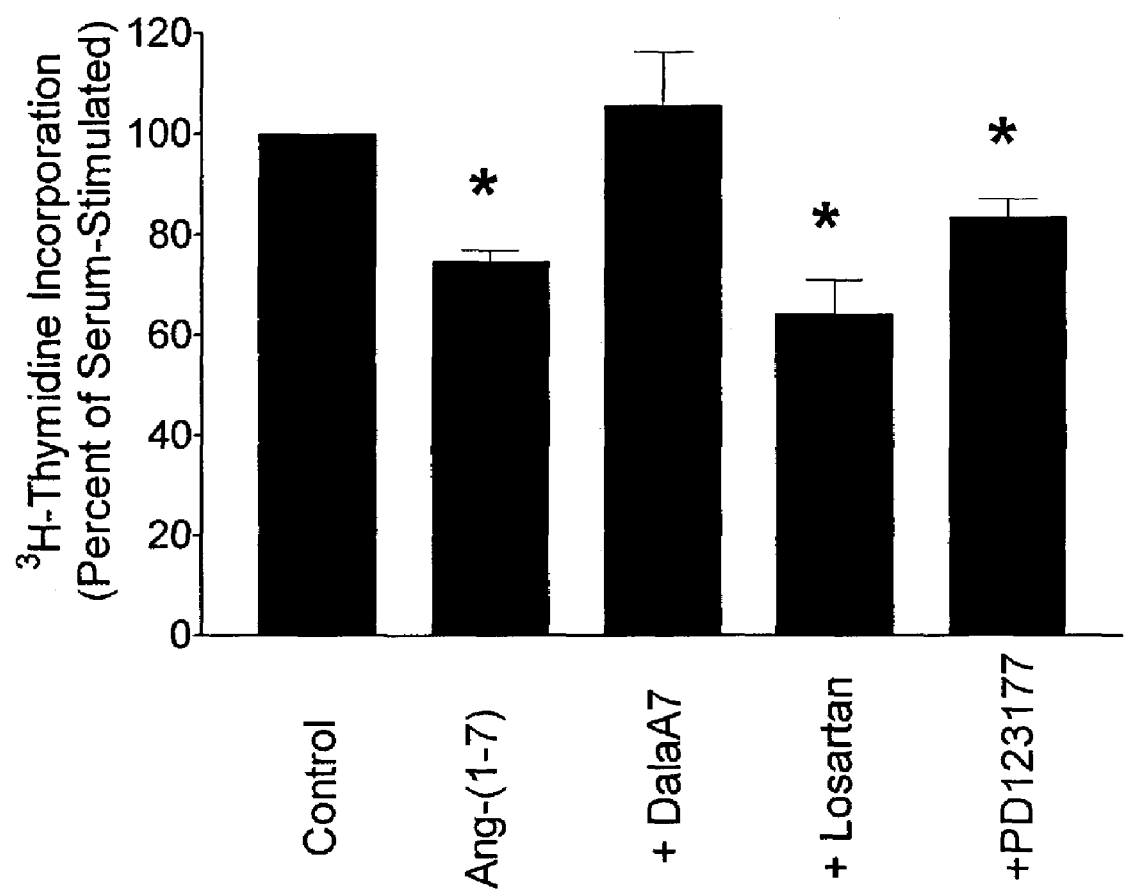
FIG. 7 shows that the Ang-(1-7)-stimulated reduction in $^3$H-thymidine incorporation into SK-LU-1 lung cancer cells is blocked by pretreatment with [D-Ala$^7$]-Ang-(1-7) (DalaA7), but not by an AT$_1$ (Losartan) or AT$_2$ (PD123177) receptor antagonist (n=3, in triplicate) in accordance with an embodiment of the present invention.

Also, in an embodiment, the inhibition of serum-stimulated growth in cancer cells is attenuated by the selective Ang-(1-7) antagonist [D-Ala$^7$]-Ang-(1-7), but not by $AT_1$ or $AT_2$ receptor antagonists (FIG. 7). Thus, inhibition of the serum-stimulated growth of SK-LU-1 human lung cancer cells by Ang-(1-7) is blocked by the Ang-(1-7) selective antagonist [D-Ala$^7$]-Ang-(1-7), while neither ATI nor $AT_2$ angiotensin receptor antagonists, Losartan and PD123177, respectively, are effective (FIG. 7). This suggests that the anti-proliferative effect of Ang-(1-7) in cancer cells is mediated by a novel $AT_{(1-7)}$ receptor.

Figure 8:
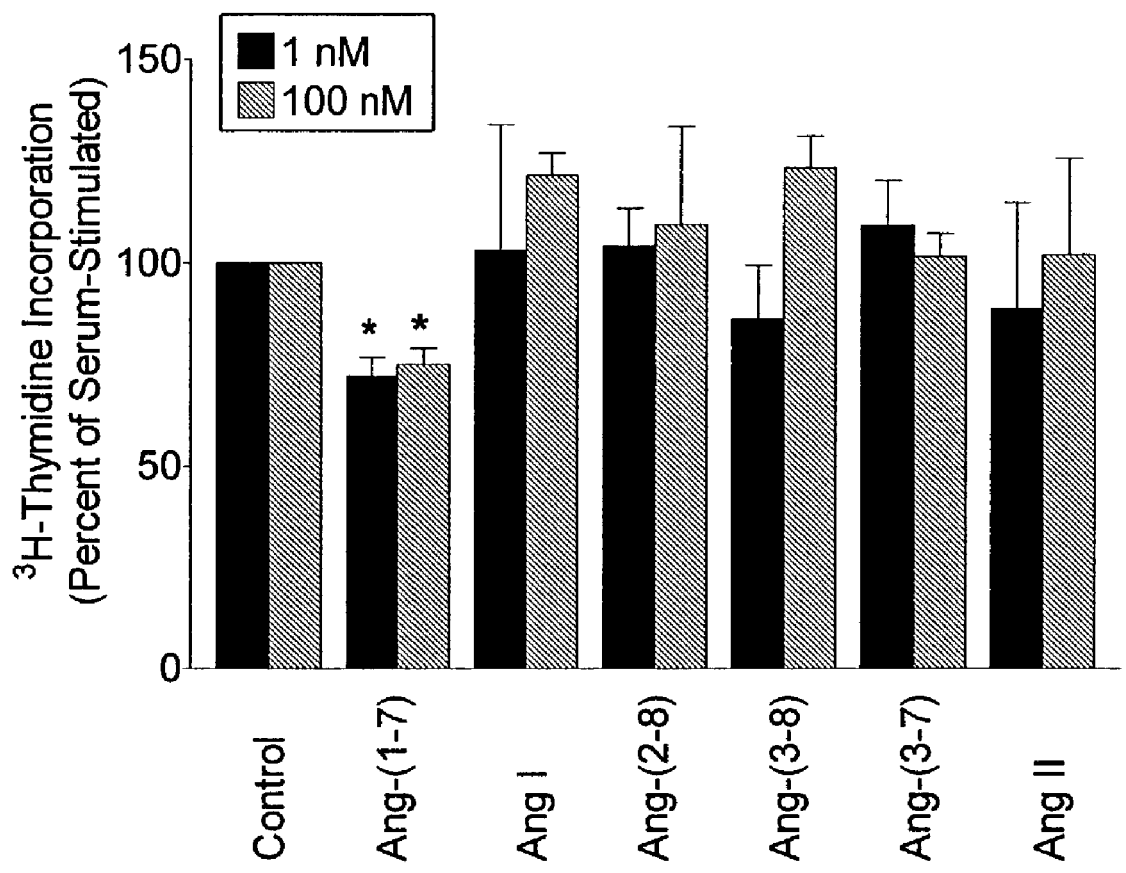
FIG. 8 shows that Ang-(1-7) (Asp-Arg-Val-Tyr-Ile-His-Pro) (SEQ ID NO: 1), at 1 or 100 nM, reduced serum-stimulated $^3$H-thymidine incorporation into SK-LU-1 lung cancer cells while Ang I (Asp-Arg-Val-Tyr-Ile-His-Pro-Phe-His-Leu) (SEQ ID NO: 4), Ang-(2-8) (Arg-Val-Tyr-Ile-His-Pro-Phe) (SEQ ID NO: 5), Ang-(3-8) (Val-Tyr-Ile-His-Pro-Phe) (SEQ ID NO: 6), Ang-(3-7) (Val-Tyr-Ile-His-Pro) (SEQ ID NO: 7) and Ang II (Asp-Arg-Val-Tyr-Ile-His-Pro-Phe) (SEQ ID NO: 8) were ineffective (n=3-9 in triplicate; * indicates p<0.05) in accordance with an embodiment of the present invention.

Also, the effects of Ang-(1-7) on cell growth and proliferation are specific to Ang-(1-7), and are not exhibited by other angiotensin peptides. Thus, neither Ang I, Ang-(2-8) or Ang III, Ang-(3-8) or Ang IV, Ang-(3-7), nor Ang II mimicked the growth inhibitor effects of Ang-(1-7), as shown in FIG. 8. These results suggest that the anti-proliferative effect of Ang-(1-7) is mediated by a novel Ang-(1-7) receptor and may represent a new therapeutic treatment for these cancers.

Figure 9:
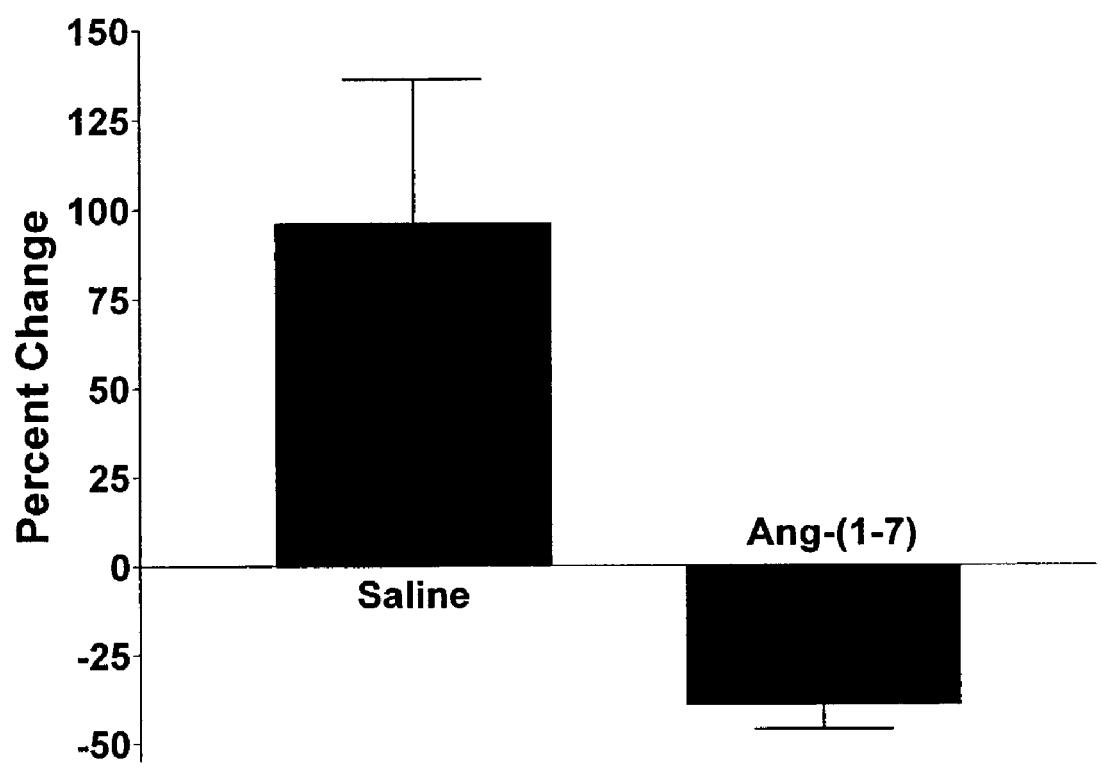
FIG. 9 shows inhibition of breast cancer tumor growth by Ang-(1-7) in accordance with an embodiment of the present invention. Tumor-bearing mice infused for 28 days with Ang-(1-7) (n=4) had a 40% reduction in tumor size, while the tumors of saline-treated animals (n=3) doubled, as compared to tumor volume prior to treatment.

The effects of Ang-(1-7) on tumor growth are also seen in vivo. In a mouse model using athymic mice injected with breast cancer cells, tumor growth is dramatically reduced upon infusion of Ang-(1-7) (24 µg/kg/hr) for 28 days. As shown in FIG. 9, an approximate 40% reduction in tumor volume is observed in mice treated with Ang-(1-7) for 4 weeks, while the tumor size doubles in the saline-treated animals, as compared to tumor size prior to treatment. These results show that Ang-(1-7) inhibits breast tumor growth in vivo and that Ang-(1-7) is an effective therapeutic agent in vivo.

Angiotensin-(1-7) and Intracellular Signaling

One major response to treatment of cells, tissues or whole animals with Ang-(1-7) is the production of prostaglandins. Thus, in an embodiment, application of a pharmaceutically effective amount of angiotensin-(1-7) or angiotensin-(1-7) receptor agonist increases prostaglandins, prostacyclins and/or intracellular cAMP.

Ang-(1-7) induces prostaglandin release from astrocytes, porcine EC, and rat, porcine and rabbit VSMC (Jaiswal, N. et al., *Hypertension*, 1992, 19:II-49-55; Jaiswal, N. et al., *Am. J. Physiol. Regul. Integr. Comp. Physiol.*, 1991, 260: R1000-R1006; Jaiswal, N. et al., *Hypertension*, 1993, 21:900-905; Jaiswal, N. et al., *Hypertension*, 1991, 17:1115-1120; Jaiswal, N. et al., *J. Pharmacol. Exp. Ther.*, 1993, 264:664-673; Muthalif, M. M. et al., *J. Pharmacol. Exp. Ther.*, 1998, 284:388-398;and Tallant, E. A. et al., *Hypertension*, 1991, 18:32-39). For example, the vasodilator response to Ang-(1-7) and the depressor component of the response to Ang-(1-7) are reduced by prior treatment with the cyclooxygenase inhibitor indomethacin, indicating that these responses were mediated by prostaglandins (Benter, I. F. et al., *Peptides*, 1993, 14, 679-684; Meng, W. and Busija, D. W., *Stroke*, 1993, 24:2041-2045;and Iyer, S. N. et al., *J. Cardiovasc. Pharmacol.*, 2000, 36:109-117).

Prostacyclin ($PGI_2$) is a type of prostaglandin. Prostacyclin is a potent vasodilator and reduces vascular growth via production of cAMP. Prostacyclin is produced by the cyclooxygenase-mediated conversion of arachidonic acid into $PGG_2/PGH_2$, which is subsequently processed by prostacyclin synthase into prostacyclin. Interestingly, the cyclooxygenase inhibitor indomethacin effectively blocks the growth inhibition mediated by Ang-(1-7).

Figure 10:
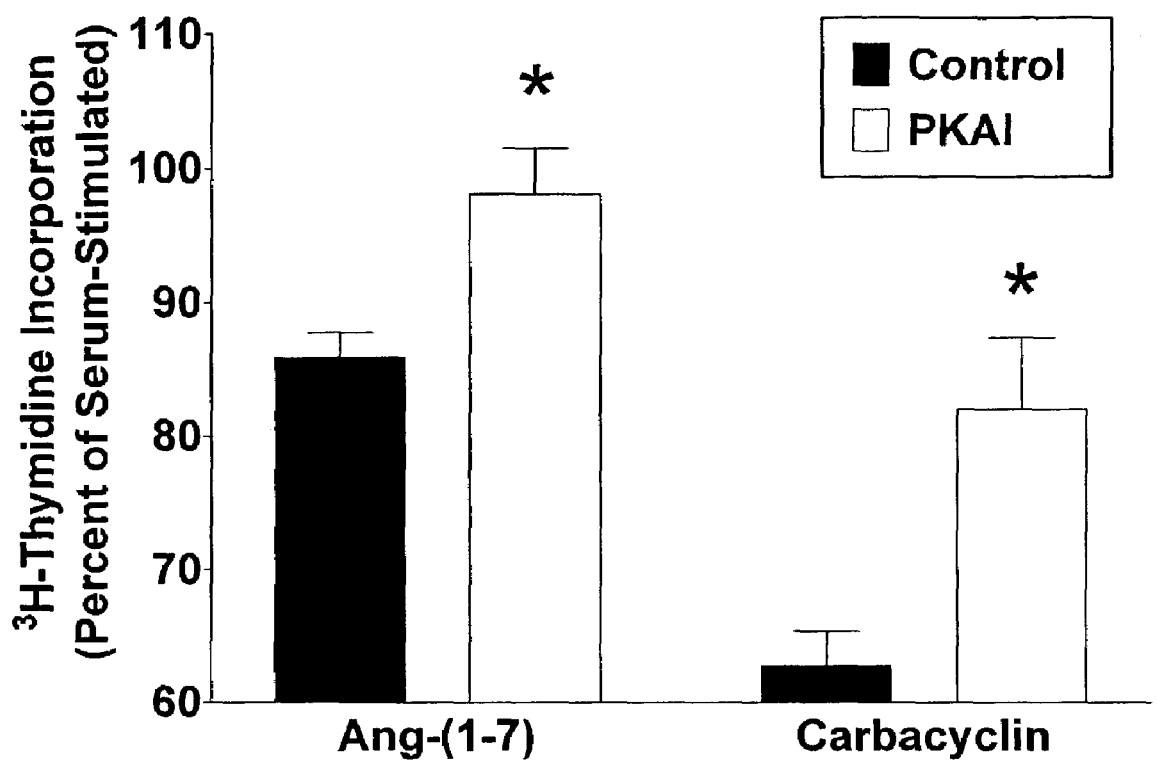
FIG. 10 shows the effect of the cAMP-dependent protein kinase inhibitor (PKAI) Rp-cAMPS (10 µM) on the inhibition of serum-stimulated $^3$H-thymidine incorporation by either 1 µM Ang-(1-7) or 5 µM carbacyclin in VSMCs in accordance with an embodiment of the present invention. The results are from VSMCs from 3 Sprague Dawley rats and each point was in triplicate.

The addition of prostacyclin (or stable analogs of prostacyclin such as carbacyclin) to VSMCs activates adenylate cyclase resulting in an elevation in the cellular levels of cAMP. Ang-(1-7), at a concentration of 1 µM, causes a significant increase in the cellular levels of cAMP, to 131.9±9.7% of basal (n=3, p<0.05), in the presence of 1 mM isobutylmethyl xanthine (IBMX), a cyclic nucleotide phosphodiesterase inhibitor. cAMP activates a cAMP-dependent protein kinase, protein kinase A. As shown in FIG. 10, the reduction in serum-stimulated $^3$H-thymidine incorporation by Ang-(1-7) or carbacyclin was completely blocked by pretreatment with the protein kinase A inhibitor (PKAI) Rp-adenosine-3',5'-cyclic monphospho-phorothioate triethylamine salt (Rp-cAMPS). These results suggest that Ang-(1-7) is directly coupled to the Gs protein to activate adenylate cyclase and elevate cellular cAMP production. Alternatively, Ang-(1-7) may stimulate the production of prostacyclin which binds to prostacyclin receptors coupled to adenylate cyclase and the synthesis of cAMP. Thus, in an embodiment, Ang-(1-7) causes an increase in the cellular levels of cAMP (directly or via prostacylin) which stimulates the cAMP-dependent protein kinase to inhibit growth.

Alternatively and/or additionally, Ang-(1-7) may inhibit cell growth by preventing the phosphorylation and activation of MAP kinases in response to mitogen stimulation. Compounds that increase the intracellular concentration of cAMP have been shown to reduce MAP kinase activity in VSMCs and fibroblasts and thereby inhibit mitogen-stimulated growth in VSMCs (Cook, S. J. and McCormick, F., *Science*, 1993, 262:1069-1072;and Wu, J. et al., *Science*, 1993, 262;1065-1068). In addition, classic growth factors, such as PDGF, epidermal growth factor, and basic fibroblast growth factor stimulate VSMC growth in vitro and in vivo. Growth stimulation by these mitogens as well as by Ang II is mediated, at least in part, through activation of MAP kinases to induce early response genes and increase transcription.

Figure 11:
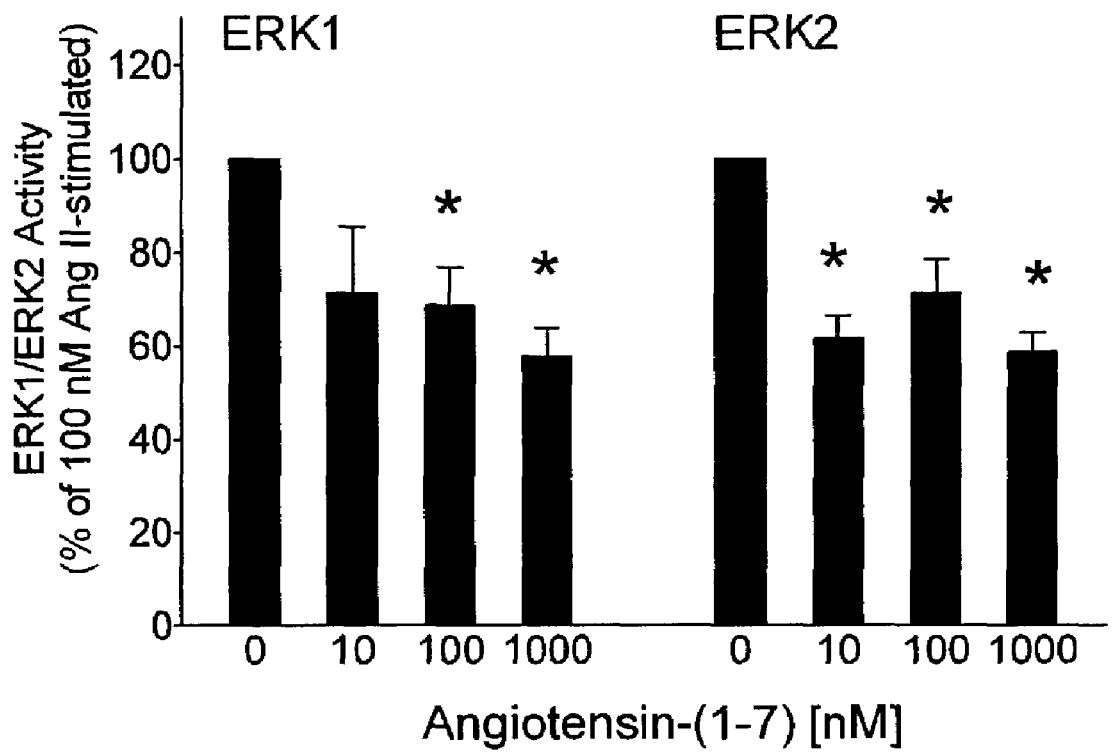
FIG. 11 shows that increasing concentrations of Ang-(1-7) causes a dose-dependent reduction in ERK1 and ERK 2 activities stimulated by 100 nM Ang II (n=VSMCs from 7 different rat aortas; * denotes p<0.05), in accordance with an embodiment of the present invention.
Figure 12:
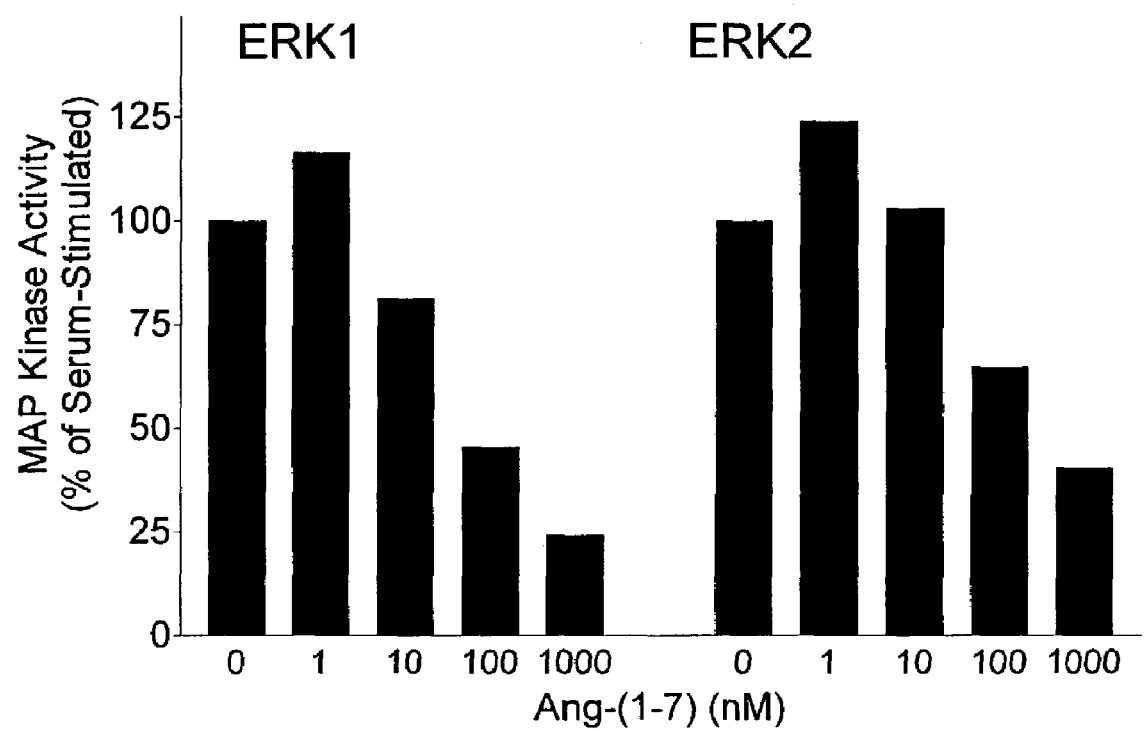
FIG. 12 shows that Ang-(1-7) causes a dose dependent reduction in serum-stimulated activation of ERK1 and ERK2 in SK-LU-1 lung cancer cells in accordance with an embodiment of the present invention. The data is representative of experiments with SK-LU-1 cells of 3 different passage numbers.

The activity of the MAP kinases ERK1 and ERK2 in VSMCs can be measured using phospho-specific antibodies that only recognize the activated protein kinases. As shown in FIG. 11, Ang-(1-7) causes a dose-dependent reduction in Ang II-stimulated ERK activity in VSMCs, with maximal inhibition at 1 IM Ang-(1-7). Similarly, Ang-(1-7) at 1 µM shows maximal inhibition of serum-stimulated ERK1 and ERK2 activation in SK-LU-1 lung cancer cells (FIG. 12).

Figure 13:
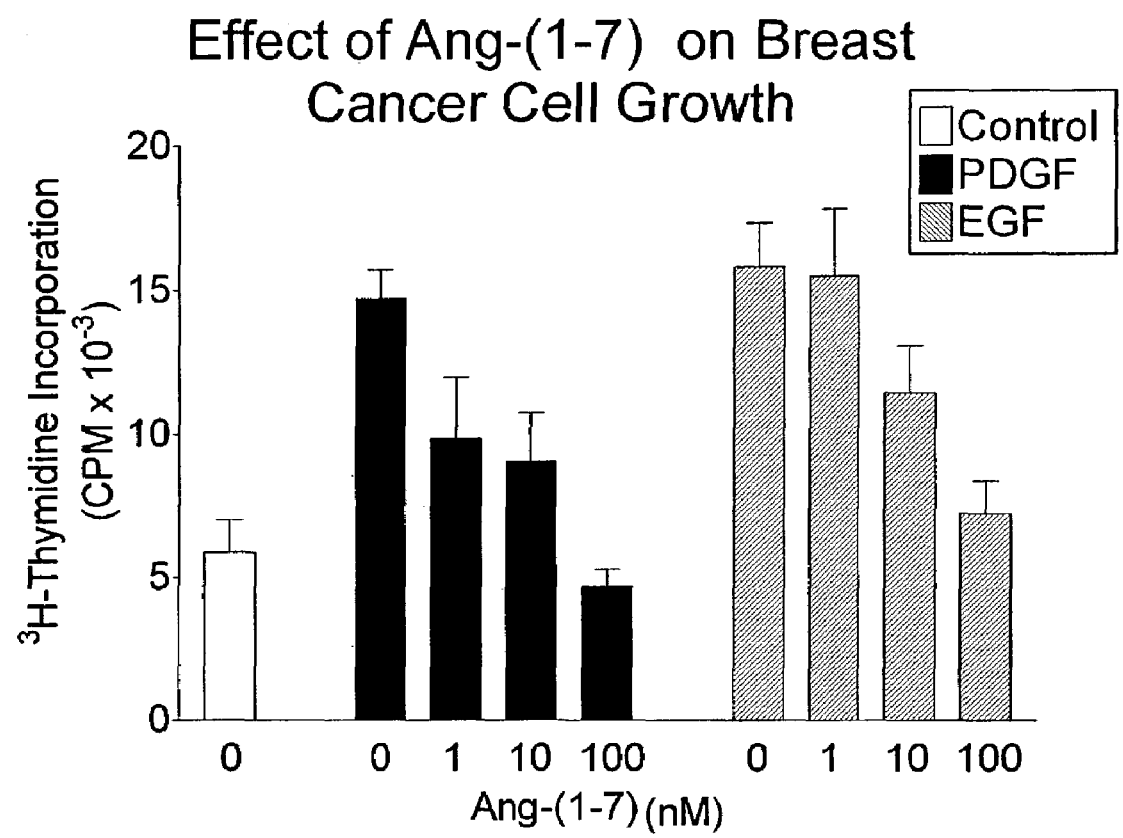
FIG. 13 shows that Ang-(1-7) inhibits platelet-derived growth factor (PDGF) or epidermal growth factor (EGF)-stimulated $^3$H-thymidine incorporation into human ZR-75-1 breast cancer cells in accordance with an embodiment of the present invention.

Ang-(1-7) also reduces ERK phosphorylation by platelet derived growth factor (PDGF). Thus, 10 ng/mL PDGF increases ERK1 and ERK2 activities by 16-fold and 26-fold in VSMCs. This stimulation is inhibited by almost 50% by 1 µM Ang-(1-7). Also, as shown in FIG. 13, Ang-(1-7) inhibits platelet-derived growth factor (PDGF) or epidermal growth factor (EGF)-stimulated $^3$H-thymidine incorporation into human ZR-75-1 breast cancer cells by at least 50% (FIG. 13).

Thus, in an embodiment, Ang-(1-7) inhibits cell growth through a reduction in the activity of mitogen-stimulated MAP kinases. Ang-(1-7) may also reduce MAP kinase activity by inhibiting the signaling pathways that stimulate MAP kinase phosphorylation or by stimulating MAP kinase phosphatase activity.

Signal Transduction and Potential Molecular Mechanisms of Inhibition of Cancer Cell Growth and Proliferation by Ang-(1-7)

Figure 14:
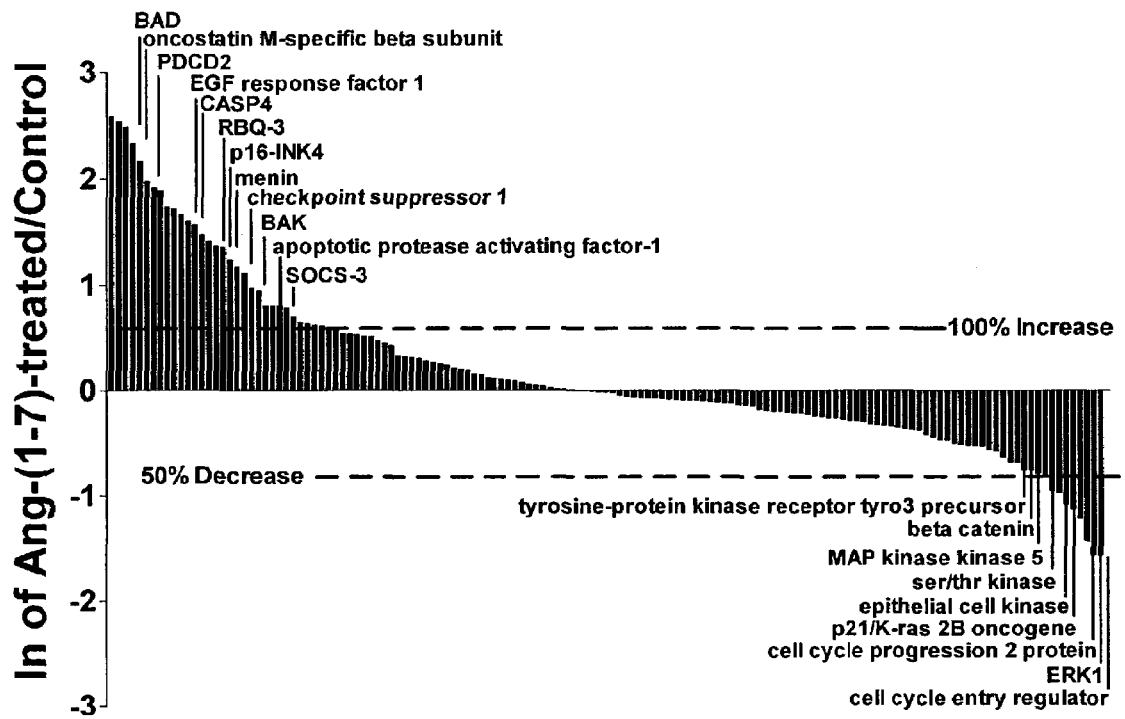
FIG. 14 shows a histogram of SK-LU-1 cells treated with Ang-(1-7) in accordance with an embodiment of the present invention. Quiescent SK-LU-1 lung cancer cells were stimulated with 1% FBS for 2 h in the presence or absence of 100 nM Ang-(1-7). Radiolabeled CDNA, prepared from DNase-treated total RNA, was incubated with Human Cancer Atlas cDNA Expression Array (Clontech Laboratories).

Cell division is a complex process that occurs with exquisite precision such that each daughter cell receives the correct number of chromosomes and is capable of independent function. Cell cycle events are initiated at the appropriate time, allowing for the completion of one phase before the next one is triggered. In an embodiment, angiotensin-(1-7) or other angiotensin-(1-7) receptor agonists inhibit cancer cell growth and/or proliferation by increasing the expression of genes involved in tumor suppression, apoptosis, and/or cell cycle inhibition. Alternatively, or additionally, angiotensin-(1-7) or other angiotensin-(1-7) receptor agonists may inhibit cancer cell growth and/or proliferation by decreasing the levels of known oncogenes, protein kinases, and/or cell cycle progression genes in the cancer. FIG. 14 shows a histogram of gene transcription increases and decreases when quiescent SK-LU-1 lung cancer cells stimulated with 1% FBS for 2 h in the presence of 100 nM Ang-(1-7) as compared to SK-LU-1 lung cancer cells stimulated with 1% FBS for 2 h in the absence of Ang-(1-7).

Cyclin-dependent kinases (CDKs) are proteins involved in the control of the cell cycle. CDKs catalyze the covalent attachment of phosphate to protein substrates, thereby altering the enzyme activity or protein affinity of the substrate. The regulation of the cellular concentrations of CDKs leads to cyclical changes in the phosphorylation of key components of the cell-cycle machinery, resulting in the initiation (or inhibition) of cell cycle events. CDKs are activated by binding to regulatory proteins called cyclins. Changes in CDK activity during the cell cycle are due primarily to the amount of cyclin proteins in the cell. In turn, cyclin concentrations are regulated at transcription and through proteolytic degradation of the cyclins at specific cell-cycle stages.

For example, two classes of CDK inhibitors-the p16/p19$^{ARF}$ and p21 families of proteins—bind to specific CDKs to prevent their interaction with cyclins and thereby interfere with cyclin/CDK regulation of the cell cycle. Thus, p16$^{INK4a}$ inhibits CDK4 and CDK6, resulting in hypophosphorylation of the retinoblastoma protein (Rb). When Rb is underphosphorylated, it binds to the transcriptional activator E2F to block transcription and prevent progression through the cell cycle. Upon phosphorylation by CDK4 and 6, hyperphosphorylated Rb releases bound E2F, allowing it to increase the transcription of genes involved in progression through the cell cycle (Lukas, J. et al., *Nature*, 1995, 375:503-506;and Serraro, M. et al., *Science*, 1995, 267:249-252).

Cell cycle control of most cell types is also responsive to extracellular signals. Classic growth factors such as platelet-derived growth factor (PDGF), epidermal growth factor (EGF), basic fibroblast growth factor (bFGF), or serum stimulate cell growth in vitro and in vivo. Growth stimulation by these mitogens is mediated, at least in part, through ras-Raf activation of mitogen-activated protein kinases (MAP kinases) to induce early response genes and increase transcription (Marrero, M. B. et al., *J. Biol. Chem.*, 1997, 272:24684-24690; Molloy, C. J. et al., *J. Biol. Chem*, 1993, 268:7338-7345;and Pelech, S. L. and Sanghera, J. S., *Science*, 1992, 257:1355-1356).

The Ras/Raf/MEK/ERK phosphorylation cascade is the prototypical cellular proliferation pathway documented in mammalian cells. Growth stimulation by many cytokines as well as by growth hormones also involves activation of the Janus kinase (JAK) family of cytosolic tyrosine kinases. Janus kinases stimulate the phosphorylation of STAT (signal transducers and activators of transcription) proteins, causing their translocation to the nucleus and subsequent activation of transcription (Marrero, M. B. et al., *J. Biol. Chem.*, 1997, 272:24684-24690;and Marrero, M. B. et al., *Nature*, 1995, 375:247-250).

Figure 15:
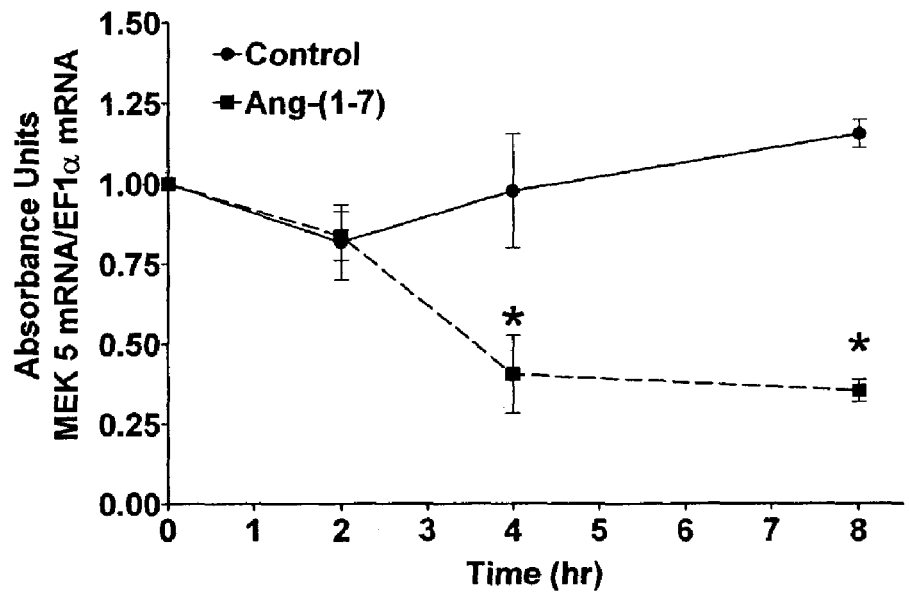
FIG. 15 shows regulation of MEK 5 mRNA and protein by Ang-(1-7) in SK-LU-1 lung cancer cells in accordance with an embodiment of the present invention.
Figure 15:
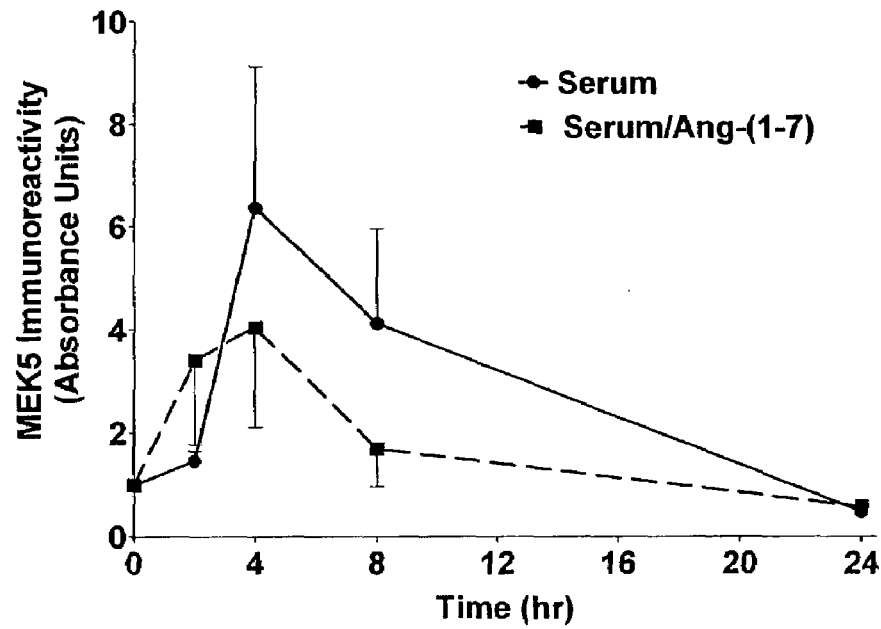

Thus, in an embodiment, application of a pharmaceutically effective amount of angiotensin-(1-7), or other angiotensin-(1-7) receptor agonists may inhibit cancer cell growth and/or proliferation by decreasing the levels of known oncogenes, protein kinases, and/or cell cycle progression genes in cancer cells. In an embodiment, the genes showing decreased expression comprise cell cycle entry regulator, ERK1, cell cycle progression 2 protein, p21/K-ras 2B oncogene, epithelial cell kinase, ser/thr kinase, MAP kinase kinase 5 (MEK5), beta catenin, tyrosine-protein kinase receptor tyro3 precursor (FIG. 14). As shown in FIG. 15, Ang-(1-7) decreases both MEK 5 mRNA and protein levels in SK-LU-1 lung cancer cells stimulated with serum. Thus, although MEK5 protein levels increased immediately following mitogen stimulation, at both 4 and 8 hours MEK5 mRNA and protein levels are reduced by treatment with Ang-(1-7).

Thus, in an embodiment, Ang-(1-7) agonists inhibit cancer cell growth by regulation of MAP kinase and JAK/STAT signaling pathways. This is supported by the findings that: (1) p21/ras mRNA and ERK1 mRNA and protein are downregulated in serum-stimulated human SK-LU-1 lung cancer cells following Ang-(1-7) treatment; (2) down-regulation of MEK5 mRNA and protein is observed in mitogen-stimulated human lung cells following treatment with Ang-(1-7); (3) Ang-(1-7) up-regulates the expression of SOCS-3, a negative regulator of the JAK/STAT pathway in human lung cancer cells (FIG. 14) (Dey, B. R. et al., *Biochem. Biophys. Res. Commun.*, 2000, 278:38-43;and Duhe, R. J. et al., *Cell Biochem. Biophys.*, 2001, 34:17-59); and (4) Ang-(1-7) inhibits tumor growth in vivo.

Alternatively and/or additionally, Ang-(1-7) agonists inhibit cancer cell growth and/or proliferation by increasing the levels of genes involved in tumor suppression and/or cell cycle inhibition. Preferably, the genes showing increased expression comprise pl6-INK, oncostatin M-specific beta subunit, PDCD2, EGF response factor 1, CASP4, RBQ-3, menin, checkpoint suppressor 1, SOCS-3, insulin-like growth factor binding protein 2, B-myb or the fau tumor suppressor (FIG. 14).

Thus, under normal conditions, tissues maintain a balance between the rates of cell proliferation and cell death. In contrast, tumor formation is a pathological state resulting from heightened cell division and a reduced rate of apoptosis. Many cancer cells manifest an enhanced resistance to physiological stimuli that would ordinarily trigger apoptosis in normal cells. Substances that can stimulate apoptosis in cancer cells may provide a novel mechanism for reducing cell number.

Caspase-3 is activated during apoptosis. In an embodiment, treatment of cancer cells with Ang-(1-7) upregulates genes encoding the pro-apoptotic proteins BAD, BAK as well as apoptotic protease activating factor 1 (FIG. 14) and increases the caspase-3 cleavage product of poly(ADP-ribose) polymerase (PARP) (FIG. 16) in mitogen-stimulated cancer cells. An increase in the amount of caspase-3 cleavage product PARP by treatment with Ang-(1-7) indicates that Ang-(1-7) stimulates apoptosis in lung cancer cells to thereby reduce cell growth.

Therapeutics

The invention contemplates methods of administration which are well known in the art. For example, in an embodiment, administration of the compound is intravenous. In another embodiment, the method of administration is by a transdermal patch. Also, administration may employ a time-release capsule. In another embodiment, administration of the compound is intra-arterial. In yet another embodiment, administration of the compound is oral or as an aerosol. In another embodiment, administration of the compound is sublingual. In yet another embodiment, administration of the drug is transrectal, as by a suppository or the like.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers, that are suitable for such formulations include the following: fillers and extenders such as starch, sugars, mannitol, and silicic derivates; binding agents such as carboxymethyl cellulose and other cellulose derivatives, alginates, gelatin, and polyvinyl pyrrolidone; moisturizing agents such as glycerol; disintegrating agents such as agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The therapeutic efficacy of exogenous compounds can be determined by standard pharmaceutical procedures in cell cultures or experimental animals using procedures known in the art. The dose ratio between toxic and therapeutic effects is the therapeutic index and may be expressed as $LD_{50}/ED_{50}$, wherein $LD_{50}$ is understood to represent the dose which is toxic to 50% of the subjects and $ED_{50}$ is understood to represent the dose which is effective in 50% of the subjects. Generally, compounds which exhibit large therapeutic indices are preferred. Administration of the compound may be hourly, daily, weekly, monthly, yearly or a single event.

In an embodiment, the dose of Ang-(1-7) agonist required for inhibition of cancer cells comprises levels of angiotensin-(1-7) agonist that are used pharmacologically in animals and humans. Also preferably, the dose of angiotensin-(1-7) receptor agonist results in a local concentration of angiotensin-(1-7) agonist at the tumor which ranges from 0.005 nM to 10 μM, and more preferably, from 0.05 nM to 1 μM, or even more preferably, from 1 nM to 100 nM. Also, the ability of Ang-(1-7) agonists to inhibit tumor growth may a function of cell division and the length of the cell cycle. Thus, application of the Ang-(1-7) agonist may be hourly, daily, or over the course of weeks. Thus, preferably, the effective amount of the Ang-(1-7) agonist comprises from about 1 ng/kg body weight to about 100 mg/kg body weight. More preferably, the effective amount of the Ang-(1-7) agonist comprises from about 1 μg/kg body weight to about 50 mg/kg body weight. Even more preferably, the effective amount of the Ang-(1-7) agonist compound comprises from about 10 μg/kg body weight to about 10 mg/kg body weight. Alternatively, a continuous level of Ang-(1-7) agonist ranging from about 0.05-1,000 μg/kg/hour, or more preferably, 0.5-250 μg/kg/hr, or even more preferably 5-50 μg/kg/hour may be employed. The actual effective amount will be established by dose/response assays using methods standard in the art. Thus, as is known to those in the art, the effective amount will depend on bioavailability, bioactivity, and biodegradability of the compound.

EXAMPLES

The present invention will be further understood by reference to the following non-limiting examples.

Example 1

Materials and Methods

A. Angiotensin Receptor Pentides and Non-peptide Compounds

All angiotensin peptides (natural and modified) were obtained from Bachem, Torrance, Calif. $AT_1$ antagonists Losartan and L158,809 were obtained from Merck & Co., Inc., Rahway, N.J. The $AT_2$ antagonist PD123177 was obtained from Parke-Davis Pharmaceutical Research, Ann Arbor, Mich.

B. Rat Vascular Smooth Muscle Cells (VSMCs) and Human Lung Cancer Cells

Vascular smooth muscle cells were isolated form 12-14 week old Sprague-Dawley rats by explant culture (Freeman, E. J. et al., Hypertension, 1996, 28:104-108). Human lung and breast cancer cell lines were obtained from American Type Tissue Culture (ATTC) and included cells of the SK-LU-1 and A549 cell lines (both of which are derived from adenocarcinomas) as well as SK-MES-1 cells (derived from non-small cell lung tumors) and ZR-75-1 breast cancer cells.

Cells were grown in DMEM with 10% fetal bovine serum (FBS), 100 μg/mL penicillin and 100 units/mL streptomycin in a humidified 37° C. incubator gassed with 5% $CO_2$ and 95% room air. Cells were grown to subconfluence in either 24-well cluster plates or 100 mm dishes and made quiescent by treatment for 48 h with serum-depleted growth media, prior to the experiments outlined below to measure cell growth ($^3$H-thymidine incorporation), cell signaling or apoptosis.

C. Analysis of $^3$H-thymidine Incorporation

To measure $^3$H-thymidine incorporation, quiescent cells were incubated with serum and angiotensin peptides for 24 h at 37° C. $^3$H-thymidine (0.25 μCi/well) was added and the cells incubated for an additional 4 h to incorporate the radiolabeled nucleotide. Subsequently, the cell monolayer was washed with cold phosphate-buffered saline (PBS; 50 mM $NaPO_4$, 120 mM NaCl, pH=7.2). The adherent cells were precipitated with cold 10% TCA (4° C. for 30 min) and dissolved in 0.2% SDS in 0.1 N NaOH. Incorporated $^3$H-thymidine was determined by liquid scintillation spectrometry, as previously described (Freeman, E. J. et al., Hypertension, 1996, 28:104-108). Growth inhibition was defined as a reduction in the amount of $^3$H-thymidine incorporation as compared to the mitogen-stimulated controls.

To study the receptor specificity of the effect, cell monolayers were preincubated with 1 μM of the $AT_1$ antagonist Losartan (or L158,809), the $AT_2$ antagonist PD 123319, the non-selective angiotensin peptide antagonist [$Sar^1$-$Thr^8$]-Ang II, or the Ang-(1-7)-selective antagonist [D-$Ala^7$]-Ang-(1-7), followed by treatment with various doses of mitogens and Ang-(1-7). Quiescent cells were stimulated with increasing concentrations of Ang-(1-7) and/or antagonists for 24 h. During an additional 4 h, cell monolayers were pulsed with $^3$H-thymidine (0.25 μCi/well) and harvested. Cells treated with mitogen and antagonists in the absence of Ang-(1-7) were used as the controls, to detect any effect of the antagonists alone.

D. Statistics

For all experiments, cells were used from at least three different passage numbers of each cell type. Values are expressed as mean±standard error of the mean. Statistical significance of differences was evaluated by one way analysis of variance with p values corrected by Dunnett's post test, using the statistics package Instat (GraphPad). The criterion for statistical significance was set at $p<0.05$.

E. RT-PCR and Western Analysis

For RT-PCR, total RNA was isolated using the Atlas Pure Total RNA Labeling System (Clontech Laboratories, Inc). The RNA concentration was quantified by UV spectroscopy and any degradation assessed by ethidium bromide staining intensity of 28S and 18S ribosomal RNA following agarose gel electrophoresis. The isolated RNA was incubated with DNase to eliminate any residual DNA, and approximately 250 ng of total RNA per sample incubated with or without AMV reverse transcriptase in a mixture containing deoxynucleotides, random hexamers, and RNase inhibitor in reverse transcriptase buffer. The mixture was heated for 5 min at 95° C. to terminate the reaction. For amplification of the resulting cDNA, 1 μmol/L gene-specific primers, 0.2 mmol/L deoxynucleotides, 5 μCi$^{32}$P-dCTP, 1.5 mmol/L MgCl$_2$, and 1.5 U Taq DNA polymerase was added to 3 μL of the RNA sample in a final volume of 50 μL. As an internal standard, primers specific for the gene encoding Elongation Factor 1α were added. Following PCR, the amplification products were separated by polyacrylamide gel electrophoresis, visualized by autoradiography, and analyzed using the MCID imaging system.

For Western blot analysis, quiescent cells treated with Ang-(1-7) and serum for various periods of time, between 2 and 24 h, were solubilized in SDS and protein content analyzed using the modified Lowry method (Lowry, O. H., et al., J. Biol. Chem., 1951, 193:265-275). Proteins were separated electrophoretically on SDS polyacrylamide gels, transferred to polyvinyl membranes, and incubated with primary antibodies to proteins of interest. Appropriate horseradish peroxidase (HRP)-conjugated second antibodies were added and immunoreactive products visualized using the enhanced chemoluminescence reagents from Amersham. The density of each immunoreactive product was quantified using the MCID imaging system. Antibodies to proteins that participate in cell signaling, apoptosis, and regulation of the cell cycle are commercially available from a variety of sources.

F. Measurement of MAP Kinases

Quiescent lung cancer cells were incubated with increasing concentrations of Ang-(1-7) [from $10^{-9}$ to $10^{-6}$ M] for 10 min at room temperature. Reactions were terminated with Triton lysis buffer (50 mM Tris-HCl, pH 7.4, 1% Triton X-100, 100 mM NaCl, 5 mM EDTA, 50 mM NaF, 0.6 μM leupeptin, 0.01 mM Na$_3$VO$_4$ and 0.1 mM PMSF) and protein concentrations determined (Lowry, O.H., et al., J. Biol. Chem., 1951, 193:265-275). Proteins were separated by SDS polyacrylamide gel electrophoresis and transferred to polyvinyl membranes. The activation and autophosphorylation of ERK1 and ERK2 was determined using antibodies specific for the phosphorylated kinases (using antibodies from Cell Signaling Technologies). The immunoreactive product were visualized by enhanced chemiluminescence (ECL, Amersham) and quantified by densitometry, using the MCID image analysis system. The phospho-MAP kinase antibodies only recognize the catalytically activated and phosphorylated forms of MAP kinase (both ERK1 and ERK2 MAP kinase). The blots were also probed with antibodies to ERK1/2, to control for protein loading.

Example 2

Inhibition of Vascular Growth by Ang-(1-7) In Vitro

These experiments support earlier indications (Freeman, E. J. et al., *Hypertension*, 1996, 28:104-108;and Tallant, E. A. et al., *Hypertension*, 1999, 34:950-957) that Ang-(1-7) inhibits the growth of cultured vascular smooth muscle cells (VSMCs). Incorporation of $^3$H-thymidine into VSMCs obtained from rat thoracic aorta was significantly increased by incubation with fetal bovine serum (FBS), platelet-derived growth factor (PDGF), or Ang II. Following a 48 hr treatment with 1 μM Ang-(1-7), the incorporation of $^3$H-thymidine in response to 1% FBS, 10 ng/mL PDGF and 100 nM Ang II was markedly attenuated (to 66.4, 84.3, and 75.8% of mitogen-stimulated activity, respectively). The reduction in serum-stimulated thymidine incorporation by Ang-(1-7) was dose-dependent, with a peak effect at a dose of 1 tM and an IC$_{50}$ of 115 nM (FIG. 1). Maximal inhibition by 1 μM Ang-(1-7) was approximately 60% of control in the presence or absence of FBS, which is similar to the growth inhibition previously reported for atrial natriuretic factor (ANF) (Appel, R. G., *Am. J. Physiol.*, 1990, 259:E312-E318).

Total cell number in response to treatment with Ang-(1-7) was also determined using a Coulter counter. The number of cells per well increased to 142% of basal following treatment with 1% serum. Treatment of serum-stimulated cells with 1 μM Ang-(1-7) significantly reduced the number of cells per well (to 109% of basal). By comparison, Ang II increased the number of cells per well to 145% of basal values and caused a dose-dependent stimulation of $^3$H-thymidine incorporation into VSMCs, as shown in FIG. 1. Thus, Ang-(1-7) inhibits mitogen-stimulated VSMC growth and opposes the proliferative effects of Ang II.

Example 3

The Effects of Ang-(1-7) Are Mediated Via a Specific Ang-(1-7) Receptor

It is documented that the mitogenic effect of Ang II is mediated by the AT$_1$ angiotensin receptor and that stimulation of vascular AT$_2$ receptors inhibits growth. However, attenuation of (fetal bovine) serum-stimulated thymidine incorporation (FBS) by Ang-(1-7) (+A7) was unaffected by antagonists selective for AT$_1$ (L158,809) or AT$_2$ (PD 123177) receptors (FIG. 2). In contrast, a 10-fold molar excess of the non-selective angiotensin receptor antagonist ([Sar$^1$-Thr$^8$]-Ang II; Sarthran) completely blocked growth inhibition by Ang-(1-7), indicating that the effect of the heptapeptide was a result of the activation of an angiotensin receptor pharmacologically distinct from either AT$_1$ or AT$_2$ receptors. [D-Ala$^7$]-Ang-(1-7) also blocked the growth inhibitory response to Ang-(1-7). The substitution of D-alanine for proline in Ang-(1-7) results in a molecule that has no agonistic activity, does not compete at AT$_1$ or AT$_2$ receptors, and selectively blocks hemodynamic and renal responses to Ang-(1-7) (Santos, R. A. S. et al., *Brain Res. Bull.*, 1994, 35:293-298). These data indicate that Ang-(1-7) inhibits VSMC growth through activation of a non-AT$_1$, non-AT$_2$ receptor that is sensitive to [Sar$^1$-Thr$^8$]-Ang II and [D-Ala$^7$]-Ang-(1-7), the AT$_{(1-7)}$ receptor.

Example 4

In Vivo Studies of Ang-(1-7) Reduction of Vascular Cell Growth

To study the role of the peptide in vivo, the effect of Ang-(1-7) on vascular growth stimulated by balloon catheter injury to the rat carotid artery was determined. Intravenous infusion of Ang-(1-7) with a chronically implanted minipump [24 μg/kg/h, 5 μL/h, 12 days] increased the plasma Ang-(1-7) concentration to 131.4±39.7 pM (n=5) from 42.2±10.7 pM (n=8) in carotid artery-injured rats infused with saline. Plasma concentrations of Ang II, blood pressure and heart rate were similar in rats infused with Ang-(1-7) or saline. Morphometric analysis of carotid artery cross-sections indicated that Ang-(1-7) infusion significantly reduced the neointimal area compared to rats infused with saline (0.10±0.009 mm$^2$ vs. 0.066±0.012 mm$^2$, respectively; p<0.05) but had no effect on the medial area of the injured or the contralateral uninjured artery as compared to saline controls (FIGS. 3 and 4) (Strawn, W. B. et al., *Hypertension*, 1999, 33:207-211 and Tallant, E. A. et al., *Hypertension*, 1999, 34:950-957). Thus, Ang-(1-7) inhibits vascular growth in vivo. The antiproliferative effect of Ang-(1-7) in preventing neointimal growth is of clinical importance as vascular re-stenosis mediated by a proliferative response of smooth muscle in blood vessels is a complication of surgical procedures that use stents to prevent vessel occlusion following crushing of an atherosclerotic plaque (angioplasty).

The concentrations of Ang-(1-7) shown to be effective in reducing vascular growth in response to injury are similar to plasma levels of Ang-(1-7) in rats following balloon catheter injury and treated with the ACE inhibitor lisinopril (20 mg/kg/day for 14 days). In lisinopril-treated rats, plasma levels of Ang-(1-7) were elevated 2.3-fold (from 42.3±6.7 pM in saline treated animals (n=10) to 99.1±6.7 pM (n=10)). In these same animals, the cross-sectional area of the neointima was reduced to 0.09±0.01 mm$^2$ as compared to 0.12±0.02 mm$^2$ in saline-treated controls (p<0.05). Thus, exogenous Ang-(1-7) infusion or treatment with the ACE inhibitor lisinopril to increase Ang-(1-7) reduced neointimal formation after vascular injury at concentrations of the peptide only two-fold higher than in saline-treated rats.

Example 5

Inhibition of Human Cancer Cell Growth by Ang-(1-7)

These experiments show that Ang-(1-7) reduces the growth of lung and breast cancer cells. Ang-(1-7) inhibited serum-stimulated $^3$H-thymidine incorporation into human lung cancer cells of the A549, SK-MES-1, and SK-LU-1 cell lines and the ZR-75-1 breast cancer cell line. The attenuation of human lung adenocarcinoma SK-LU-1 cell growth was dependent on the dose of Ang-(1-7) with a maximal reduction of 33.8±5.3% of serum-stimulated growth and an IC$_{50}$ of 0.05 nM, as shown in FIG. 5. Ang-(1-7) also attenuated mitogen-stimulated growth of human lung adenocarcinoma A549 cells (maximal inhibition of 41.3±10.9%, IC$_{50}$=0.11 nM) as well as non-small cell lung cancer SK-MES-1 cells (maximal inhibition of 40.9±2.9%, IC$_{50}$=0.4 nM) and breast cancer ZR-75-1 cells (maximal inhibition of 37.2±6.1; IC$_{50}$=0.02 nM). Thus, Ang-(1-7) reduces human lung and breast cancer cell growth in a dose-dependent manner with IC$_{50}$ levels similar to circulating levels of Ang-(1-7) measured after treatment of rats with the ACE inhibitor lisinopril (Campbell, D. J. et al., *Hypertension*, 1993, 22:513-522; and Kohara, K. et al., *Circulation*, 1991, 84 (supp. II):662).

The inhibition of growth by Ang-(1-7) was also dependent upon the time of treatment with Ang-(1-7). The incorporation of $^3$H-thymidine into SK-LU-1, A549, and SK-MES-1 lung cancer cells and ZR-75-1 breast cancer cells stimulated to grow by the inclusion of 1% FBS was progressively reduced by daily addition of 100 nM Ang-(1-7), as shown in FIG. 6. Ang-(1-7) was renewed daily due to the endogenous degradation of the peptide (Chappell, M. C. et al., *Hypertension*, 1998, 31:362-367). These results suggest that Ang-(1-7), an endogenous peptide, inhibits the mitogen-stimulated growth of lung cancer cells.

Inhibition of the serum-stimulated growth of SK-LU-1 human lung cancer cells by Ang-(1-7) was blocked by the Ang-(1-7) selective antagonist [D-Ala$^7$]-Ang-(1-7), while neither AT$_1$ nor AT$_2$ angiotensin receptor antagonists Losartan and PD123177, respectively, were effective (FIG. 7). This suggests that the anti-proliferative effect of Ang-(1-7) in lung cancer cells is mediated by a novel AT$_{(1-7)}$ receptor.

Also the effects are specific to Ang-(1-7), and are not exhibited by other angiotensin peptides. Thus, neither Ang I, Ang-(2-8) or Ang III, Ang-(3-8) or Ang IV, Ang-(3-7), nor Ang II mimicked the growth inhibitor effects of Ang-(1-7), as shown in FIG. 8. These results suggest that the anti-proliferative effect of Ang-(1-7) is mediated by a novel Ang-(1-7) receptor and may represent a new therapeutic treatment for these cancers.

Example 6

Inhibition of Tumor Growth by Ang-(1-7)

To determine whether Ang-(1-7) inhibits tumor growth in vivo, athymic mice were inoculated subcutaneously in the lower flank with approximately 1.5×10$^7$ cells of the ZR-75-1 breast cancer cell line. Tumor volumes were measured by caliper two times per week and calculated using the formula for a semiellipsoid. After 40 days, the mice had tumors approximately 175 mm$^3$ in size and were randomized for treatment. Primed osmotic mini-pumps (delivery rate of 0.25 μL/hr) were implanted onto the backs of the mice with the control group receiving continuous intravenous infusion of saline (6 μL/24 hr) and the experimental group receiving Ang-(1-7) (24 μg/kg/hr) for 28 days. The dose of Ang-(1-7) was based on previous studies with rats, which indicated that this dose was tolerated with no change in weight, blood pressure, or heart rate and resulted in a 2 to 3-fold elevation in circulating Ang-(1-7) (Strawn, W. B. et al., *Hypertension*, 1999, 33:207-211. As shown in FIG. 9, an approximate 40% reduction in tumor volume was observed in mice treated with Ang-(1-7) for 4 weeks, while the tumor size doubled in the saline-treated animals, as compared to tumor size prior to treatment. These results show that Ang-(1-7) inhibits breast tumor growth in vivo and that Ang-(1-7) is an effective therapeutic agent in vivo.

Example 7

Mechanism of Growth Inhibition by Ang-(1-7)

It was found that Ang-(1-7) stimulates prostacyclin (PGI$_2$) release from VSMCs isolated from Sprague-Dawley rat aortas, measured as the release of the stable metabolite of prostacyclin, 6-keto-PGF$_{1\alpha}$. Ang-(1-7) caused a dose-dependent release of prostacyclin, with maximal release of 177.9±25.2% above basal release at 100 nM Ang-(1-7).

Since prostacyclin inhibits VSMC growth, these results suggest that Ang-(1-7) attenuates vascular growth through the production and release of prostacyclin.

Prostacyclin is produced by the cyclooxygenase-mediated conversion of arachidonic acid into $PGG_2/PGH_2$, which is subsequently processed by prostacyclin synthase into prostacyclin. Interestingly, the cyclooxygenase inhibitor indomethacin (IND, 10 µM) effectively blocked the growth inhibition mediated by Ang-(1-7) (97.4±3.6% of control, n=4, p<0.05) compared to the decrease of serum-stimulated $^3$H-thymidine incorporation by Ang-(1-7) in the absence of indomethacin (79.1±5.1% of total, n=5, p<0.05). Since neither a lipoxygenase inhibitor nor the cytochrome P450 inhibitor 1 7-octadecynoic acid had any effect on growth inhibition by the heptapeptide, these results show that Ang-(1-7) inhibits VSMC growth through the production of a metabolite of the cyclooxygenase pathway which may be prostacyclin.

The addition of prostacyclin or carbacyclin (5 µM; Calbiochem, La Jolla Calif.) (a stable analogs of prostacyclin) to VSMCs activates adenylate cyclase resulting in an elevation in the cellular levels of cAMP. Ang-(1-7), at a concentration of 1 µM, caused a significant increase in the cellular levels of cAMP, to 131.9±9.7% of basal (n=3, p<0.05), in the presence of 1 mM isobutylmethyl xanthine (IBMX), a cyclic nucleotide phosphodiesterase inhibitor. cAMP activates a cAMP-dependent protein kinase, protein kinase A. As shown in FIG. 10, the reduction in serum-stimulated $^3$H-thymidine incorporation by Ang-(1-7) or carbacyclin was completely blocked by pretreatment with the protein kinase A inhibitor (PKAI) Rp-adenosine-3',5'-cyclic monphosphophorothioate triethylamine salt (Rp-cAMPS) (Calbiochem, La Jolla Calif.). These results suggest that Ang-(1-7) is directly coupled to the Gs protein to activate adenylate cyclase and elevate cellular cAMP production. Alternatively, Ang-(1-7) may stimulate the production of prostacyclin which binds to prostacyclin receptors coupled to adenylate cyclase and the synthesis of cAMP. Collectively, these results suggest that Ang-(1-7) causes an increase in the cellular levels of cAMP which stimulates the cAMP-dependent protein kinase to inhibit growth.

Ang-(1-7) may inhibit cell growth by preventing the phosphorylation and activation of MAP kinases in response to mitogen stimulation. For example, compounds that increase the intracellular concentration of cAMP have been shown to reduce MAP kinase activity in VSMCs and fibroblasts and inhibit mitogen-stimulated growth in VSMCs (Cook, S. J. and McCormick, F., *Science*, 1993, 262:1069-1072;and Wu, J. et al., *Science*, 1993, 262;1065-1068). In addition, classic growth factors, such as PDGF, epidermal growth factor, and basic fibroblast growth factor stimulate VSMC growth in vitro and in vivo. Growth stimulation by these mitogens as well as by Ang II is mediated, at least in part, through activation of MAP kinases to induce early response genes and increase transcription.

The activity of the MAP kinases ERK1 and ERK2 in VSMCs was measured using phospho-specific antibodies that only recognize the activated protein kinases. Ang II caused a dose-dependent increase in both ERK1 and ERK2 phosphorylation (37- and 166-fold increase over basal), with maximal stimulation by 1 µM Ang II. Incubation of VSMCs with concentrations of Ang-(1-7) up to 1 µM had no effect on ERK1 or ERK2 phosphorylation. However, pre-incubation with increasing concentrations of Ang-(1-7) caused a dose-dependent reduction in Ang II-stimulated ERK activity, with maximal inhibition at 1 µM Ang-(1-7). One micromolar Ang-(1-7) reduced 100 nM Ang II-stimulated ERK1 and ERK2 activation by 42.3±6.2% and 41.2±4.2%, p<0.01, respectively, as shown in FIG. 11.

Ang-(1-7) also reduced ERK phosphorylation by 10 ng/mL PDGF in VSMCs, which increased ERK1 and ERK2 activities by 16-fold and 26-fold over basal, respectively. It was found that 1 µM Ang-(1-7) decreased PDGF-stimulated ERK1 and ERK2 activities by 43.6±8.6% and 38.7±11.4%, p<0.05, respectively.

To begin to address the molecular mechanisms of Ang-(1-7) inhibition of the growth of cancer cells, MAP kinase activity was measured in quiescent SK-LU-1 cells stimulated with 1% FBS, in the presence and absence of increasing concentrations of Ang-(1-7). As shown in FIG. 12, Ang-(1-7) caused a dose-dependent decrease in the amount of serum-stimulated ERK1 and ERK2 activities. These results suggest that Ang-(1-7) either inhibits the kinase which phosphorylates and activates ERK1 and ERK2, a MAP kinase kinase, or stimulates the activity of a MAP kinase phosphatase, either of which would result in a decrease in active MAP kinase.

Ang-(1-7) also inhibited platelet-derived growth factor (PDGF)- or epidermal growth factor (EGF)-stimulated $^3$H-thymidine incorporation into human breast cancer cells of the ZR-75-1 cell line, as shown in FIG. 13. For these experiments, semi-confluent cell monolayers were made quiescent by a 48-h incubation in serum-free media, followed by a 28-h treatment period with increasing concentrations of Ang-(1-7) in the presence of either 2.5 ng/mL PDGF or 100 ng/ml EGF. It was found that Ang-(1-7) reduces mitogen-stimulated human breast cancer cell growth in a dose-dependent manner.

The results show that Ang-(1-7) attenuates MAP kinase activation by either Ang II, serum, or growth factors PDGF or EGF, and that Ang-(1-7) can inhibit cell growth through a reduction in the activity of mitogen-stimulated MAP kinases. Thus, Ang-($^1$-7) may reduce MAP kinase activity by inhibiting the signaling pathways that stimulate MAP kinase phosphorylation or by stimulating MAP kinase phosphatase activity.

Example 8

Mechanisms of Inhibition of Cancer Cell Growth by Ang-(1-7)

To further assess transcriptional regulation involved in the inhibition of cancer cell growth and proliferation by Ang-(1-7), total RNA isolated from SK-LU-1 cells treated with 1% serum in the presence and absence of 100 nM Ang-(1-7) was analyzed using gene array hybridization. Cells were incubated for 2 or 8 h, and total RNA was isolated using the Atlas Pure Total RNA Labeling System (Clontech Laboratories, Inc). The RNA concentration was quantified by UV spectroscopy and any degradation was assessed by ethidium bromide staining intensity of 28S and 18S ribosomal RNA following agarose gel electrophoresis. RNA isolated from seven different cell passages was pooled prior to gene array analysis to account for individual variability in gene regulation. Radiolabeled cDNA, prepared from the pooled RNAs using the Atlas system, was incubated with DNase to degrade any residual DNA and then hybridized to the Human Cancer 1.2 Atlas CDNA Expression Array (Clonetech Laboratories, Inc). This gene array set contains 1,176 characterized human cDNAs on positively-charged nylon membranes. The resultant hybridization signals, visualized by phosphorimage analysis, were quantified using the computerized MCID imaging system with gene array analysis software to identify potential gene products which are up-regulated or down-regulated in response to Ang-(1-7) stimulation.

FIG. 14 shows some of the results obtained by gene array hybridization. A number of genes involved in tumor suppression, apoptosis, and cell cycle inhibition were upregulated in SK-LU-1 cells treated with Ang-(1-7), including the tumor suppressors p16$^{INK4a}$ and menin and genes encoding the proapoptotic proteins BAD and BAK as well as apoptotic protease activating factor 1. In contrast, several oncogenes, protein kinase and cell cycle progression genes were downregulated. For example, MAP kinase kinase 5 (MEK5), ERK1, and p21/K-ras 2B were reduced, suggesting that Ang-(1-7) may also chronically reduce the Ras/Raf/MEK/MAP kinase signaling cascade. These results suggest a number of signaling pathways that may be involved in the Ang-(1-7)-mediated reduction of cell proliferation observed in the lung cancer cells. Several candidate genes were selected for verification by RT-PCR and Western analysis.

The gene array hybridization results indicated that MAP kinase kinase 5 (MEK5) was downregulated in response to Ang-($^1$-7). Thus, MEK5 expression in SK-LU-1 lung cancer cells in response to Ang-(1-7) was measured by RT-PCR and Western analysis. Quiescent SK-LU-1 cells were stimulated with 1% serum in the presence and absence of 10 nM Ang-(1-7). RNA was isolated using Trizol and whole cell lysates were isolated at 2, 4, 8 and 24 h following treatment. As shown in FIG. 15, MEK5 mRNA and protein were reduced 4 and 8 h following treatment with Ang-(1-7). The results of these experiments indicate that the cellular concentrations of MEK5, a protein involved in MAP kinase signaling and cell growth, are reduced in human lung cancer cells following treatment with Ang-(1-7). In FIG. 15, intensities of RT-PCR products and protein bands were determined by image analysis. MEK5 protein levels increased immediately after mitogen stimulation. Still, at both 4 and 8 hours, MEK5 mRNA and protein levels are reduced by treatment with Ang-(1-7).

Figure 16:
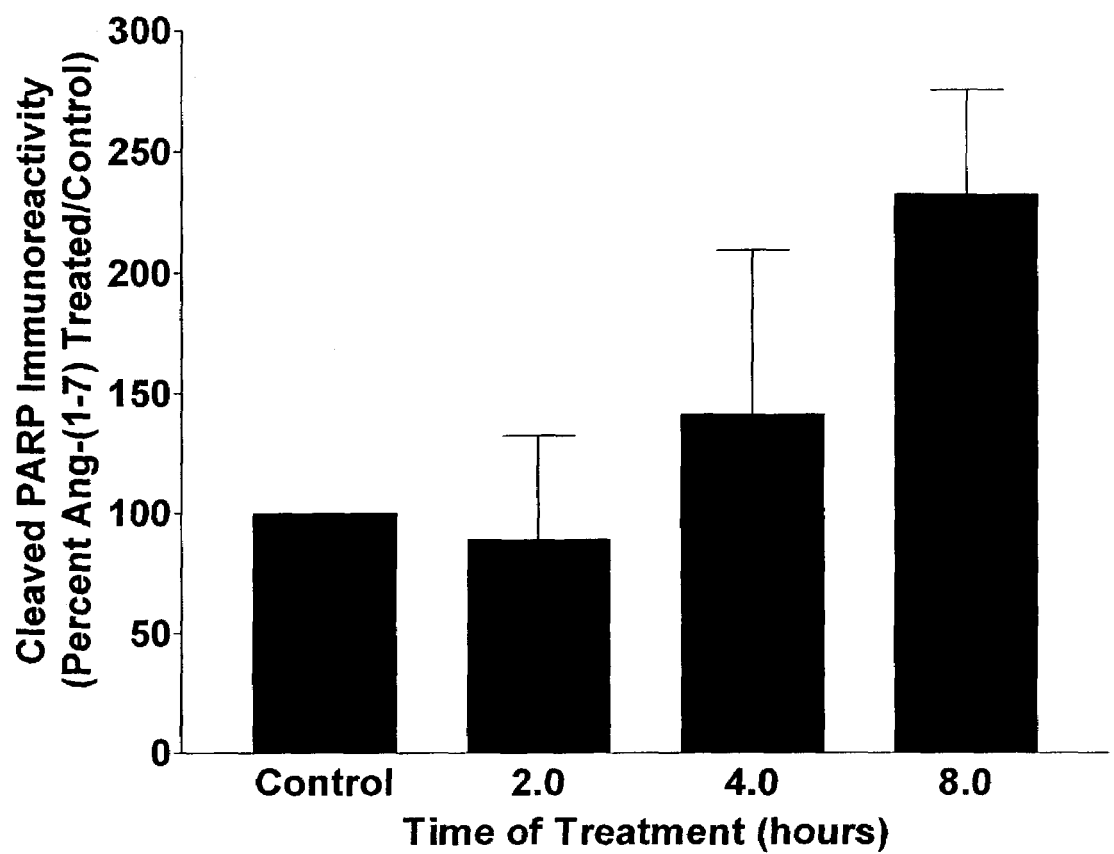
FIG. 16 shows that Ang-(1-7) stimulates apoptosis in mitogen-stimulated SK-LU-1 lung cancer cells as evidenced by an increase in the caspase-3 cleavage product poly(ADP-ribose) polymerase (PARP) as measured using an antibody specific to cleaved PARP in serum stimulated SK-LU-1 cells treated for either 2, 4, or 8 h with 10 nM Ang-(1-7) in accordance with an embodiment of the present invention.

The gene array hybridization results also indicated that mRNAs encoding proteins that stimulate or participate in apoptosis (BAD, BAK, and APAF) are upregulated by Ang-(1-7) in mitogen-stimulated SK-LU-1 cells. Stimulation of apoptosis by Ang-(1-7) was measured by generation of the caspase-3 cleavage product poly(ADP-ribose) polymerase (PARP), to determine whether Ang-(1-7) stimulates apoptosis. Since casepase-3 is activated during apoptosis, an increase in the generation of its cleavage product (PARP) is a measure of apoptosis. Cleaved PARP was measured using an anti-cleaved product-specific antibody in serum-stimulated SK-LU-1 cells treated for either 2, 4, or 8 hours with 10 nM Ang-(1-7). As shown in FIG. 16, an increase in the amount of cleaved PARP was visualized following a 4 to 8 hour treatment with Ang-(1-7), suggesting that Ang-(1-7) stimulates apoptosis. These results suggest that, in human lung cancer cells, Ang-(1-7) stimulates apoptosis to reduce cell growth.

The regulation of cell growth is a key element in the normal maintenance of healthy tissue. A delicate balance exists between the proliferative and anti-proliferative factors controlling cell growth. The identification of the molecular mechanisms regulating cell growth is vital to understanding tumor formation, and the development of anti-cancer therapeutices. In an embodiment, the present invention recognizes that Ang-(1-7), a peptide hormone present in the circulation, causes a marked decrease in cell proliferation of vascular cells as well as cancer cell growth in vitro and in vivo. Ang-(1-7) is present in the circulation at concentrations similar to the vasoconstrictor peptide hormone Ang II, and is generated from the precursor Ang I or Ang II by tissue peptidases and ACE inhibitors. Thus, in an embodiment, the present invention describes the use of a pharmaceutically effective amount of angiotensin-(1-7) or an angiotensin-(1-7) receptor agonist as a means to prevent tumor formation, or inhibit tumor growth in an individual. The invention has been described in detail with particular reference to preferred embodiments thereof, but it will be understood that variations and modifications can be effected within the spirit and scope of the invention.

What is claimed is:

1. A composition for inhibition of at least one of cancer cell growth or proliferation comprising a pharmaceutically effective amount of an agonist for the angiotensin-(1-7) receptor in a pharmaceutically acceptable carrier formulated for delivery of the agonist to the angiotensin-(1-7) receptor on the cancer cells, wherein the angiotensin-(1-7) receptor agonist comprises angiotensin-(1-7) peptide having the amino acid sequence set forth in SEQ ID NO: 1, and wherein a pharmaceutically effective amount of angiotensin-(1-7) receptor agonist comprises an amount determined to be sufficient to inhibit cancer cell growth or proliferation by binding to the angiotensin-(1-7) receptor on the cancer cell, and ranges from 0.01 nM to 100 nM angiotensin-(1-7).

2. The composition of claim 1, wherein the cancer cells comprise breast cancer, brain cancer, colon cancer, or lung cancer cells.

3. The composition of claim 1, wherein the cancer cells are in a human subject.

4. The composition of claim 1, wherein the angiotensin-(1-7) receptor agonist is modified to increase its chemical stability in vivo.

5. The composition of claim 1, wherein the pharmaceutically effective amount of the angiotensin-(1-7) receptor agonist increases cellular prostacyclins in the cancer cells.

6. The composition of claim 1, wherein the pharmaceutically effective amount of the angiotensin-(1-7) receptor agonist increases cellular cAMP in the cancer cells.

7. The composition of claim 1, wherein the pharmaceutically effective amount of the angiotensin-(1-7) receptor agonist increases the expression of at least one gene involved in tumor suppression, apoptosis, and/or cell cycle inhibition in the cancer cells.

8. The composition of claim 7, wherein the gene showing increased expression comprises a gene encoding BAD, oncostatin M-specific beta subunit, PDCD2, EGF response factor 1, CASP4, RBQ-3, p16-INK, menin, checkpoint suppressor 1, BAK, apoptotic protease activating factor-1, SOCS-3, insulin-like growth factor binding protein 2, B-myb or the fau tumor suppressor.

9. The composition of claim 1, wherein the pharmaceutically effective amount of the angiotensin-(1-7) receptor agonist decreases the levels of expression of at least one known oncogene, protein kinase gene, and/or cell cycle progression gene in the cancer cells.

10. The composition of claim 9, wherein the gene showing decreased expression comprises a gene encoding a cell cycle entry regulator, ERK1, cell cycle progression 2 protein, p21/K-ras 2B oncogene, epithelial cell kinase, ser/thr kinase, MAP kinase kinase 5 (MIEK5), beta catenin, tyrosine-protein kinase receptor tyro3 precursor, protein phosphatase 2A B56-alpha, cyclin-dependent kinase regulatory subunit (CDC28), cell division protein kinase 6 (CDK6), c-myc oncogene, ERBB-3 receptor protein tyrosine kinase, A-kinase anchoring protein, or rho C.

11. The composition of claim 1, wherein the amount of angiotensin-(1-7) receptor agonist ranges from 0.1 nM to 100 nM.

12. The composition of claim 1, wherein the amount of angiotensin-(1-7) receptor agonist ranges from 1 nM to 100 nM.

13. The composition of claim 1, wherein the amount of angiotensin-(1-7) receptor agonist ranges from 10 nM to 100 nM.

14. A kit for inhibiting at least one of cancer cell growth or proliferation in an individual comprising:
(a) at least one container comprising a pharmaceutically effective amount of a functional agonist for the angiotensin-(1-7) receptor, wherein the agonist for the angiotensin-(1-7) receptor comprises angiotensin-(1-7) peptide having the sequence set forth in SEQ ID NO: 1, and wherein a pharmaceutically effective amount comprises an amount of angiotensin-(1-7) receptor agonist determined to be sufficient to inhibit cancer cell growth or proliferation by binding to an angiotensin-(1-7) receptor on the cancer cell and ranges from 0.01 nM to 100 nM angiotensin-(1-7);
(b) a pharmaceutically acceptable carrier formulated for delivery of the agonist to the angiotensin-(1-7) receptor on the cancer cell; and
(c) instructions for use.

15. The kit of claim 14, wherein the cancer cells comprise, breast cancer, brain cancer, colon cancer, or lung cancer cells.

16. The kit of claim 14, wherein the angiotensin-(1-7) receptor agonist is modified to increase its chemical stability in vivo.

17. The kit of claim 14, wherein the amount of angiotensin-(1-7) receptor agonist ranges from 0.1 nM to 100 nM.

18. The kit of claim 14, wherein the amount of angiotensin-(1-7) receptor agonist ranges from 1 nM to 100 nM.

19. The kit of claim 14, wherein the amount of angiotensin-(1-7) receptor agonist ranges from 10 nM to 100 nM.

* * * * *

UNITED STATES PATENT AND TRADEMARK OFFICE
CERTIFICATE OF CORRECTION

PATENT NO. : 7,375,073 B2
APPLICATION NO. : 10/375733
DATED : May 20, 2008
INVENTOR(S) : E. Ann Tallant, Patricia E. Gallagher and Carlos M. Ferrario It is certified that error appears in the above-identified patent and that said Letters Patent is hereby corrected as shown below:

In the Specification

Column 1, Line 13:
Insert -- GOVERNMENT RIGHTS
This invention was made with government support under RO018370, CA103098, HL051952, CA012197, and HL079498 awarded by the National Institutes of Health. The government has certain rights in the invention. --

Signed and Sealed this
Ninth Day of May, 2023

Katherine Kelly Vidal
*Director of the United States Patent and Trademark Office*

SEQUENCE LISTING

```
<160> NUMBER OF SEQ ID NOS: 8

<210> SEQ ID NO 1
<211> LENGTH: 7
<212> TYPE: PRT
<213> ORGANISM: Homo sapiens

<400> SEQUENCE: 1

Asp Arg Val Tyr Ile His Pro
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Sarcosine

<400> SEQUENCE: 2
```

```
Xaa Arg Val Tyr Ile His Pro Thr
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa = D-Alanine

<400> SEQUENCE: 3

Asp Arg Val Tyr Ile His Xaa
1               5

<210> SEQ ID NO 4
<211> LENGTH: 10
<212> TYPE: PRT
<213> ORGANISM: Homo sapiens

<400> SEQUENCE: 4

Asp Arg Val Tyr Ile His Pro Phe His Leu
1               5                   10

<210> SEQ ID NO 5
<211> LENGTH: 7
<212> TYPE: PRT
<213> ORGANISM: Homo sapiens

<400> SEQUENCE: 5

Arg Val Tyr Ile His Pro Phe
1               5

<210> SEQ ID NO 6
<211> LENGTH: 6
<212> TYPE: PRT
<213> ORGANISM: Homo sapiens

<400> SEQUENCE: 6

Val Tyr Ile His Pro Phe
1               5

<210> SEQ ID NO 7
<211> LENGTH: 5
<212> TYPE: PRT
<213> ORGANISM: Homo sapiens

<400> SEQUENCE: 7

Val Tyr Ile His Pro
1               5

<210> SEQ ID NO 8
<211> LENGTH: 8
<212> TYPE: PRT
<213> ORGANISM: Homo sapiens

<400> SEQUENCE: 8

Asp Arg Val Tyr Ile His Pro Phe
1               5
```